(12) United States Patent
Beeson, IV et al.

(10) Patent No.: US 8,703,452 B2
(45) Date of Patent: Apr. 22, 2014

(54) EXTRACELLULAR ALDONOLACTONASE

(71) Applicant: The Regents of the University of California, Oakland, CA (US)

(72) Inventors: William T. Beeson, IV, Indianapolis, IN (US); James H. Dounda Cate, Berkeley, CA (US); Michael A. Marletta, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/051,402

(22) Filed: Oct. 10, 2013

(65) Prior Publication Data

US 2014/0038245 A1 Feb. 6, 2014

Related U.S. Application Data

(63) Continuation of application No. 13/813,153, filed as application No. PCT/US2011/041704 on Jun. 23, 2011, now Pat. No. 8,569,022.

(60) Provisional application No. 61/369,358, filed on Jul. 30, 2010.

(51) Int. Cl.
*C12P 7/58* (2006.01)
(52) U.S. Cl.
USPC ...................................................... 435/137
(58) Field of Classification Search
USPC ...................................................... 435/137
See application file for complete search history.

(56) References Cited

U.S. PATENT DOCUMENTS

2008/0206815 A1 8/2008 Brown et al.

OTHER PUBLICATIONS

Altschul et al., "Gapped BLAST and PSI-BLAST: A New Generation of Protein Database Search Programs", Nucleic Acids Research, vol. 25, No. 17, 1997, pp. 3389-3402.
Bendtsen et al., "Improved Prediction of Signal Peptides: SignalP 3.0", J. Mol. Biol., vol. 340, 2004, 783-795.
Bhat et al., "Sporotrichum Thermophile Growth, Cellulose Degradation, and Cellulase Activity", Applied and Environmental Microbiology, vol. 53. No. 9, Sep. 1987, pp. 2175-2182.
Canevascini et al., "Cellobiose Dehydrogenases of *Sporotrichum (Chrysosporium) thermophile*", Eur. J. Biochem, vol. 198, 1991, pp. 43-52.
Claeyssens et al., "Fungal Cellulase Systems : Comparison of the Specificities of the Cellobiohydrolases Isolated from *Penicillium pinophilum* and *Trichoderma reesei*", Biochem J., vol. 261, 1989, 819-825.
Collard et al., "Identification of the cDNA Encoding Human 6-Phosphogluconolactonase, the Enzyme Catalyzing the Second Step of the Pentose Phosphate Pathway1", FEBS Letters, vol. 459, 1999, pp. 223-226.

Conchie et al., "Inhibition of Glycosidases by Aldonolactones of Corresponding Configuration", Biochem. J., vol. 65, 1957, pp. 389-395.
Dereeper et al., "Phylogeny.Fr: Robust Phylogenetic Analysis for the Non-Specialist", Nucleic Acids Research, vol. 36, Apr. 19, 2008, pp. W465-W469.
Finn et al., "The Pfam Protein Families Database", Nucleic Acids Research, vol. 38, 2010, pp. D211-D222.
Hager et al., "The *Pseudomonas aeruginosa* devB/SOL Homolog, pgl, Is a Member of the hex Regulon and Encodes 6-Phosphogluconolactonase", Journal of Bacteriology, vol. 182, No. 14, Jul. 2000, pp. 3934-3941.
Henikoff et al., "Amino Acid Substitution Matrices from Protein Blocks", Proc. Natl.. Acad. Sci. USA, Biochemistry, vol. 89, Nov. 1992, pp. 10915-10919.
Hestrin, Shlomo, "The Reaction of Acetylcholine and Other Carboxylic Acid Derivatives with Hydroxylamine and its Analytical Application", Journal of Biological Chemistry, vol. 180, Feb. 24, 1949, pp. 249-261.
Kajander et al., "The Structure of *Neurospora crassa* 3-Carboxy-cis,cis-Muconate Lactonizing Enzyme, Aβ Propeller Cycloisomerase", Structure, vol. 10, Apr. 2002, pp. 483-492.
Kupor et al., "6-Phosphogluconolactonase Mutants of *Escherichia coli* and a Maltose Blue Gene", Journal of Bacteriology, vol. 100, No. 3, Dec. 1969, pp. 1296-1301.
Li et al., "Mapping Short DNA Sequencing Reads and Calling Variants using Mapping Quality Scores", Genome Research, vol. 18, 2008, pp. 1851-1858.
Margolin et al., "Improved Plasmids for Gene Targeting at the his-3 Locus of *Neurospora crassa* by Electroporation", Fungal Genetics Newsletter, 1997, 4 pages.
Mazur et al., "3-Carboxy-cis,cis-Muconate Lactonizing Enzyme from *Neurospora crassa*: An Alternate Cycloisomerase Motif", Journal of Bacteriology, vol. 176, No. 6, Mar. 1994, pp. 1718-1728.
Mortazavi et al., "Mapping and Quantifying Mammalian Transcriptomes by RNA-Seq", Nature Methods, vol. 5, No. 7, Jul. 2008, pp. 621-628.
Notredame et al., "T-Coffee: A Novel Method for Fast and Accurate Multiple Sequence Alignment", J. Mol. Biol., vol. 302, 2000, pp. 205-217.
Parry et al., "Biochemical Characterization and Mechanism of Action of a Thermostable β-Glucosidase Purified from *Thermoascus aurantiacus*", Biochem. J., vol. 353, 2001, pp. 117-127.
Perlack et al., "Biomass as Feedstock for a Bioenergy and Bioproducts Industry: The Technical Feasibility of a Billion-Ton Annual Supply", Environmental Sciences Division, Oak Ridge National Laboratory, Oak Ridge, TN 37831-0062, Apr. 2005, 78 pages.
Tarighi et al., "The PA4204 Gene Encodes a Periplasmic Gluconolactonase (PpgL) which is Important for Fitness of *Pseudomonas aeruginosa*", Microbiology, vol. 154, 2008, pp. 2979-2990.

(Continued)

*Primary Examiner* — Maryam Monshipouri
(74) *Attorney, Agent, or Firm* — Morrison & Foerster LLP

(57) ABSTRACT

The present disclosure relates to hydrolysis of hexose-δ-lactones by use of an *S. thermophile* extracellular aldonolactonase. In particular the present disclosure relates to compositions including a *S. thermophile* extracellular aldonolactonase and methods of use thereof.

16 Claims, 10 Drawing Sheets

(56) References Cited

OTHER PUBLICATIONS

Thomason et al., "Identification of the *Escherichia coli* K-12 ybhE Gene as pgl, Encoding 6-Phosphogluconolactonase", Journal of Bacteriology, vol. 186, No. 24, Dec. 2004, pp. 8248-8253.

Tian et al., "Transcriptional Profiling of Cross Pathway Control in *Neurospora crassa* and Comparative Analysis of the Gcn4 and CPC1 Regulons", Eukaryotic Cell, vol. 6, No. 6, Jun. 2007, pp. 1018-1029.

Westermark et al., "Cellobiose:Quinone Oxidoreductase, A New Wood-Degrading Enzyme from White-rot Fungi", Acta Chemica Scandinavica, vol. B-28, No. 2, 1974, pp. 209-214.

Zimenkov et al., "*Escherichia coli* ORF ybhE is pgl Gene Encoding 6-Phosphogluconolactonase (EC 3.1.1.31) that has no Homology with known 6PGLs from other Organisms", FEMS Microbiology Letters, vol. 244, 2005, pp. 275-280.

Invitation to Pay Additional Fees received for PCT Patent Application No. PCT1US2011/041704, mailed on Nov. 15, 2011, 2 pages.

International Search Report and Written Opinion received for PCT Patent Application No. PCT/US2011/041704, mailed on Apr. 10, 2012, 14 pages.

Beeson IV et al., "Extracellular Aldonolactonase from *Myceliophthora thermophila*", Applied and Environmental Microbiology, vol. 77, No. 2, Jan. 2011, pp. 650-656.

Beeson et al., "UniProtKB accession E5LEX3", Document Available at <http://www.uniprot.org/uniprotJE5LEX3.txt? version=1>, retrieved on Jan. 4, 2012, 1 page.

Birren et al., "GenBank Accession EAQ88010.4", Document Available at < http://www.ncbi.nlm.nih.gov/protein/EAQ88010.1>, retrieved on Jan. 5, 2012 1 page.

Driessel, Brian Van, "Bioremediation of a Bleach Plant Effluent from the Pulp and Paper Industry", University of the Free State, Bloemfontein, RSA, Nov. 2003, 178 pages.

Galagan et al., "GenBank Accession No. XP_960326, Hypothetical protein NCU07143 [Neurosporacrass a OR74A]", Document Available at <http://www.ncbi.nlm.nih.gov/protein/XP_960326.1>, retrieved on Nov. 4, 2011, 2 pages.

Genbank: CAP71345.1, "unnamed protein product [*Podospora anserina* S mat-F]", Jun. 2, 2010, 3 pages Tian et al., "Systems analysis of plant cell wall degradation by the model filamentous fungus *Neurospora crassa*", Proceedings of the National Academy of Science USA, vol. 106, No. 52, Dec. 29, 2009, pp. 22157-22162.

Notice of Allowance received for U.S. Appl. No. 13/813,153, mailed on Jun. 19, 2013. 11 pages.

Cellodextrin    Aldonolactone    Aldonic acid

Production of Biofuels

```
MRTSYGVAFALSAGFRLATAAPVCGGGSASDLLWVTTYPAGEGAQGKLLTLKLDGSKLVV
AESDTCGPYPSWLTQAGDVLYCVDEAWGGDRGTLHSLKINDDHSFTNLSQHETVGGPVST
VIYGKDGLGLAVADYAGGGIDTFNIADPAAIKLIKSLVYPAPTDGLPDPQNSARPHEAIL
DPTGEILVFPDLGADQIRVLKVDKETLEYVEKPSYTDFDRGTGPRHEAFFKSGDKTFFYL
VGELSNLLQGFSVAYNDDDSLTFTRIHNSTTHGDDKPLPEDTAAAELWIAPGSNFLTLSS
RFESSLEYTVANGTKVPSDPLITFSIDKETGALTHVQSAPAGGINPRHFSFNSDGTRVAS
ALQSDGRVVVFERDPSTGKIGKATAEGDVEGMPNFATFKQ
```

FIG. 2

```
MSPVTQLLAAAALALAPGALGAHLIASHFSGTVYSLSFTSSSNSTGTLSVTSETDGCGAT
PAWLQLYSDTGKVYCFDESWLGSGSSAEYKIADDGSLFLTGTLQPTGNSVHGALYGGADS
KGFVATVEYTPSTLTTYKMPFGGGQRLALEKFTMEGQGPNPRQDVPHPHEAQIDPTGNIM
VVPDLGADLLEVFRINAETGELTACSEGQAGPGIGPRHIVFWKNAEGLQKAYVVNELGNS
VSAWDVEYPEDDDDEAAAGGCLALNKTQTLSTYEPGTSGGPTTKAAEIRVVGNFLYASN
RADETFGPGQDSIATYTIDEQTGELAWLGAANSYSYYPRTFKFNRDGTLVAVGGQTSSNV
AIIARDPDTGKLGNLVANLEVGRKGRAGQEDGLSAVVWVQ
```

FIG. 3

```
MVHLLSNLLVGLALAPSALGATLLVSHFSGPVYTLSLTTSGTTGKLSITSQAGGCGTTPA
WLEYYNDTKTAYCFDESWTGSSVITQYKVGSDGRLTQSGQTRFSGNTVHGKVYGSSDGKG
FIATAQYSPSTITTYKLPLGQSQVQLEKFTMSQRGPNSRQDVPHPHETQIDPTGKPMLVP
DLGADLIRIFKIDASTGRLTACPAGQASPGIGPRHAQWWKSADGVLRLYTLNELGNSVSS
WNVVYPTDSNGCLALSRAQTLSTYAPGKEGGPTTKAAEIRVAGNFLYASNKADQTFGSNQ
DSVAIYTIDHQTGGIAWKEAANSYSYYPRTFDINKDGTLVAFGGQTSSNVAIVSRDPATG
KLGNLVANLQVGNKGRAGEEDGLSAVVWVE
```

EXTRACELLULAR ALDONOLACTONASE

CROSS-REFERENCE TO RELATED APPLICATION

This application is a continuation of U.S. patent application Ser. No. 13/813,153, now U.S. Pat. No. 8,569,022, which is a U.S. National Phase Patent Application of PCT/US2011/041704, filed Jun. 23, 2011, which claims the benefit of U.S. Provisional Application No. 61/369,358, filed Jul. 30, 2010, each of which is hereby incorporated by reference, in its entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 677792000601SeqList.txt, date recorded: date: Oct. 10, 2013, size: 28 KB).

FIELD

The present disclosure relates to hydrolysis of hexose-δ-lactones by use of an *S. thermophile* extracellular aldonolactonase. In particular the present disclosure relates to compositions including an *S. thermophile* extracellular aldonolactonase and methods of use thereof.

BACKGROUND

Lignocellulosic biomass is an abundant renewable resource and a potential feedstock for the production of liquid fuels and other value-added products (1). The principal barriers to the production of lignocellulose-derived biofuels are the high costs of chemical pretreatment and enzymes for depolymerization (2). The thermophilic fungus, *Sporotrichum thermophile*, very rapidly degrades cellulose, and metabolizes powdered cellulose and glucose at nearly same rates (3). The thermostability of the hydrolytic enzymes from this organism provides practical advantages, such as high enzymatic activity over a broad pH range, over those from the mesophilic fungus, *Hypocrea jecorina* (syn. *Trichoderma reesei*), which has traditionally been used for production of biomass degrading enzymes. During growth on cellulosic substrates, *S. thermophile* secretes cellulases, hemicellulases (4), oxidative enzymes (5), and many proteins of unknown function.

Cellobiose dehydrogenase (CDH) is an extracellular hemo-flavoprotein that is produced in large amounts by *S. thermophile* during growth on cellulose (5). CDH is produced by many cellulolytic fungi (6). It oxidizes the reducing end of cellobiose and longer cellodextrins to the corresponding aldonolactones (FIG. 1). For all cellulolytic microorganisms, the sugar acid yield from cellulose could be improved by increasing the expression level of CDH and glucose oxidases.

Aldonolactones, or sugar lactones, are unstable in aqueous solution and undergo hydrolysis to form the corresponding aldonic acids. The extent and rate of uncatalyzed hydrolysis are dependent on the specific lactone, pH, and temperature. The equilibrium constant between glucono-δ-lactone and gluconic acid is 7.7, favoring gluconic acid, and the half-life of glucono-δ-lactone in water at room temperature and pH 5.0 is approximately 1 hour (10). However, despite this lack of stability, fungi such as *S. thermophile* have evolved enzymes to catalyze the hydrolysis of sugar lactones to their corresponding aldonic acids. This hydrolysis to aldonic acid increases susceptibility of cellulose to subsequent hydrolysis by cellulolytic enzymes such as cellulases. Therefore, efficient conversion of sugar lactones to aldonic acids can have beneficial effects on cellulose degradation and, thus, on biofuel formation (FIG. 1).

Enzymatic hydrolysis of sugar lactones has been mostly studied in the context of the pentose phosphate pathway (11-14). In the pentose phosphate pathway glucose-6-phosphate is converted to 6-phospho-gluconolactone by glucose-6-phosphate dehydrogenase. The lactone is then hydrolyzed by 6-phosphogluconlactonase (PGL) to generate 6-phosphogluconate and finally converted to ribulose-5-phosphate. In glycolysis-deficient strains of *Escherichia coli*, deletion of the PGL gene leads to severe inhibition of growth on glucose (15), clearly demonstrating that spontaneous hydrolysis of 6-phosphogluconolactone is insufficient in vivo.

There have been reports of aldonolactonase activity secreted into the culture filtrates of diverse fungi (16-17). An aldonolactonase from *Aspergillus niger* was purified by Bruchmann et al. (16) and was shown to be an important part of the fungal cellulolytic system. However, extracellular aldonolactonases have not been purified, identified, or characterized from *S. thermophile*.

Reactions at high temperatures and acidic pH values are critical for the enzymatic conversion of plant cell wall polysaccharides to fermentable sugars in the emerging biofuel industry. High temperature conversions lower the risk of bacterial contamination and enzymes usually have faster turnover at high temperatures. Low pH is also beneficial because of the reduced risk of contamination. Cellulases work optimally at pH 4.8-5.0 and it makes the process easier if all the enzymes have similar pH optima so they can be used simultaneously. Thus, it is important in the art to have thermostable enzymes isolated from thermophilic fungi, such as *S. thermophile*, that are active over a broad range of pH values for the hydrolysis of lactones produced during the conversion of biofuel feedstock plant cell wall polysaccharides to fermentable sugars. Compositions and methods comprising aldonolactonases active over a broad range of pH values will find utility in the enzymatic depolymerization of lignocellulose.

BRIEF SUMMARY

The present disclosure relates to recombinant polypeptides with conserved motifs and lactonase activity, such as *Sporotrichum thermophile* aldonolactonase 1, variants thereof, and fragments thereof. The present disclosure further relates to compositions including a polypeptide with conserved motifs and aldonolactonase activity and food additives containing these compositions. Moreover, the present disclosure relates to methods for the production of lactonic acid by hydrolysis of hexose-containing poly- or oligosaccharides, methods of deconstructing biomass, methods of food processing, methods of textile cleaning, and methods of paper pulp bleaching, by using such compositions. The present disclosure further relates to host cells containing a recombinant polypeptide, which has conserved motifs and lactonase activity, and compositions containing these host cells.

Thus, one aspect provides recombinant polypeptides containing a GPRH motif (SEQ ID NO: 9) and a DPTGxF/Y motif (SEQ ID NO: 10) where the polypeptide has lactonase activity. In certain embodiments, the recombinant polypeptide contains the amino acid sequence of SEQ ID NO: 1. In certain embodiments, the recombinant polypeptide contains the amino acid sequence of SEQ ID NO: 2. In certain embodiments, the recombinant polypeptide contains the amino acid sequence of SEQ ID NO: 3.

Another aspect of the invention provides compositions containing the recombinant polypeptide according to the preceding aspect in any of its embodiments. In certain embodiments, the composition further contains at least one additional polypeptide. In certain embodiments that may be combined with the preceding embodiment, the at least one additional polypeptide is cellobiose dehydrogenase (CDH). In other embodiments that may be combined with the preceding embodiment having the composition further contain at least one additional polypeptide, the at least one polypeptide is glucose oxidase (GOX).

Yet another aspect of the invention provides an expression vector containing, operably linked to a regulatory sequence, a polynucleotide sequence encoding the polypeptide according to the preceding aspect having the recombinant polypeptide.

Another aspect of the invention provides compositions containing the expression vector according to the preceding aspect.

Still another aspect of the invention provides host cells containing the expression vector according to the preceding aspect. In certain embodiments, the host cell is selected from the group consisting of a fungal cell, an yeast cell, a bacterial cell, an insect cell, and a mammalian cell.

Another aspect of the invention provides compositions containing the host cells according to the preceding aspect in any of its embodiments.

Still another aspect provides methods of producing a recombinant polypeptide including: (a) providing a population of host cells containing a vector, where the vector contains a polynucleotide sequence encoding a polypeptide, which contains a GPRH motif (SEQ ID NO: 9) and a DPT-GxF/Y motif (SEQ ID NO: 10) and has lactonase activity; and (b) culturing the population of cells under conditions in which the polypeptide encoded by the coding sequence of the expression vector is expressed. In certain embodiments, the polypeptide contains the amino acid sequence of SEQ ID NO: 1. In other embodiments, the polypeptide contains the amino acid sequence of SEQ ID NO: 2. In certain embodiments, the polypeptide contains the amino acid sequence of SEQ ID NO: 3. In certain embodiments, the host cell is selected from the group consisting of a fungal cell, an yeast cell, a bacterial cell, an insect cell, and a mammalian cell.

Another aspect provides methods of producing aldonic acid including contacting a hexose-δ-lactone substrate with a recombinant polypeptide containing a GPRH motif (SEQ ID NO: 9) and a DPTGxF/Y motif (SEQ ID NO: 10) and having lactonase activity. In certain embodiments, the recombinant polypeptide contains the amino acid sequence of SEQ ID NO: 1. In other embodiments, the recombinant polypeptide contains the amino acid sequence of SEQ ID NO: 2. In certain embodiments, the recombinant polypeptide contains the amino acid sequence of SEQ ID NO: 3. In certain embodiments, the hexose-δ-lactone substrate is selected from the group consisting of cellobiono-δ-lactone, glucono-δ-lactone, and lactono-δ-lactone.

Still another aspect provides methods of degrading biomass including contacting the biomass with the composition according to the preceding aspect having a recombinant polypeptide containing a GPRH (SEQ ID NO: 9) and a DPT-GxF/Y motif (SEQ ID NO: 10) and having lactonase activity. In certain embodiments, the composition further includes CDH.

Yet another aspect provides methods of deconstructing biomass including contacting the biomass with the composition according to the preceding aspect having a recombinant polypeptide containing a GPRH (SEQ ID NO: 9) and a DPT-GxF/Y motif (SEQ ID NO: 10) and having lactonase activity in order to deconstruct the biomass. In certain embodiments, the biomass contains plant material. In certain embodiments that may be combined with the preceding embodiment, the plant material is selected from the group consisting of miscanthus, switchgrass, cord grass, rye grass, reed canary grass, common reed, wheat straw, barley straw, canola straw, oat straw, corn stover, soybean stover, oat hulls, oat spelt, sorghum, rice hulls, sugarcane bagasse, corn fiber, barley, oats, flax, wheat, linseed, citrus pulp, cottonseed, groundnut, rapeseed, sunflower, peas, lupines, palm kernel, coconut, konjac, locust bean gum, gum guar, soy beans, Distillers Dried Grains with Solubles (DDGS), Blue Stem, corncobs, pine, conifer softwood, eucalyptus, birchwood, willow, aspen, poplar wood, hybrid poplar, energy cane, short-rotation woody crop, crop residue, yard waste, or a combination thereof.

Another aspect provides methods of food processing including contacting a plant material with the composition according to the preceding aspect having a recombinant polypeptide containing a GPRH (SEQ ID NO: 9) and a DPT-GxF/Y motif (SEQ ID NO: 10) and having lactonase activity to yield digestible plant material. In certain embodiments, the digestible plant material is fed to animals.

Another aspect provides food additives containing the composition according to the preceding aspect having a recombinant polypeptide containing a GPRH (SEQ ID NO: 9) and a DPTGxF/Y motif (SEQ ID NO: 10) and having lactonase activity.

Yet another aspect provides methods of textile cleaning including contacting a soiled textile with the composition according to the preceding aspect having a recombinant polypeptide containing a GPRH (SEQ ID NO: 9) and a DPT-GxF/Y motif (SEQ ID NO: 10) and having lactonase activity to yield clean textile.

Another aspect provides methods of paper pulp bleaching containing contacting paper pulp with the composition according to the preceding aspect having a recombinant polypeptide containing a GPRH (SEQ ID NO: 9) and a DPT-GxF/Y motif (SEQ ID NO: 10) and having lactonase activity to yield bleached paper pulp.

BRIEF DESCRIPTION OF THE DRAWINGS

FIG. 2 depicts the amino acid sequence of *S. thermophile* extracellular aldonolactonase 1 (Spoth11109678) (SEQ ID NO: 1). The capped residues depict the signal peptide, double-underlined regions depict predicted N-linked glycosylation sites, and underlined regions depict peptides detected by LC-MS. The residues circled appear to be conserved in aldonolactonases.

FIG. 3 depicts the amino acid sequence of *S. thermophile* extracellular aldonolactonase 2 (Spoth1189286) (SEQ ID NO: 2). The residues circled appear to be conserved in aldonolactonases.

FIG. 4 depicts the amino acid sequence of *N. crassa* lactonase 2 (NCU01743) (SEQ ID NO: 3). The residues circled appear to be conserved in aldonolactonases.

FIG. 10 depicts a multiple sequence alignment of *S. thermophile* extracellular aldonolactonase 1 (Spoth11109678) with other aldonolactonases. Full solid circle indicates a residue in the predicted active site of NC_cmle. ST_1 is *S. thermophile* extracellular aldonolactonase 1 (Spoth11109678; SEQ ID NO: 1), PA_1; *Podospora anserina* aldonolactonase 1 (XP_001910211.1; SEQ ID NO: 4), TR is *Trichoderma reesei* (Trire2155887; SEQ ID NO: 5), AN is *Aspergillus niger* (XP_659716.1; SEQ ID NO: 6), ST_2 is *Sporotrichum thermophile* extracellular aldonolactonase 2 (Spoth1189286; SEQ ID NO: 2), EC_pgl is *Escherichia coli* 6-phosphogluconolactonase (NP_415288.1; SEQ ID NO: 7), and NC_cmle is *Neurospora crassa* cis-carboxymuconate-lactonizing enzyme (XP_957686; SEQ ID NO: 8). There appears to be two conserved motifs in the aldonolactonases: a GPRH motif (SEQ ID NO: 9) (amino acids 224-227 in *S. thermophile* aldonolactonase 1) and a DPTGxF/Y (SEQ ID NO: 10) (amino acids 182-187 in *S. thermophile* aldonolactonase 1).

Definitions

Figure 1:
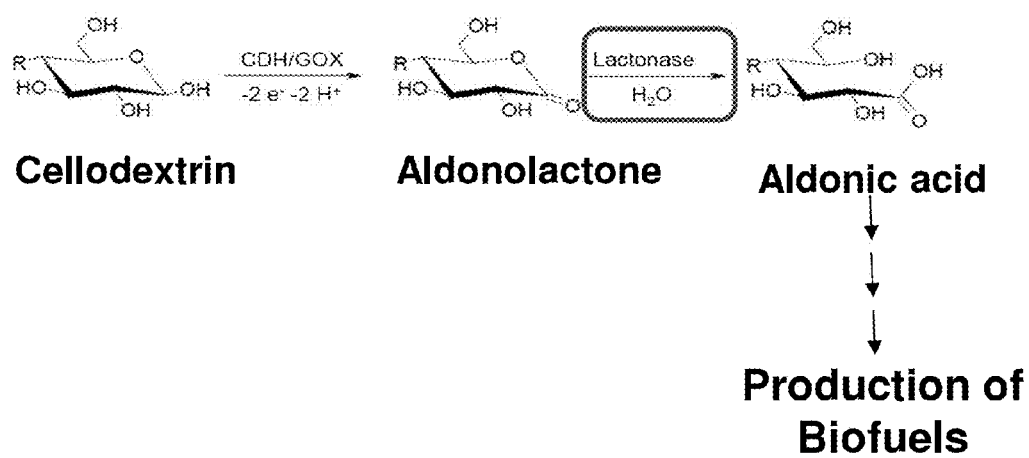
FIG. 1 provides a schematic representation of a mechanism of the extracellular sugar oxidation and lactone hydrolysis. Reducing sugars are initially converted to sugar lactones by extracellular oxidizing enzymes, including glucose oxidase (GOX) and cellobiose dehydrogenase (CDH). Conversion to the corresponding sugar acid is catalyzed by extracellular lactonases (boxed). This conversion to aldonic acid eases subsequent steps in cellulose degradation and therefore increases efficiency of biofuel production.

The terms "extracellular aldonolactonase," "aldonolactonase," "*S. thermophile* aldonolactonase 1," "*S. thermophile* aldonolactonase 1," and "lactonase" refer to an enzyme capable of catalyzing the hydrolysis of aldonate and aromatic lactones to the corresponding carboxylic acids (EC 3.1.1.17). In particular, "aldonolactonases" convert hexose-δ-lactones to their corresponding aldonic acids.

The term "catalytic activity" or "activity" describes quantitatively the conversion of a given substrate under defined reaction conditions. The term "specific activity" describes quantitatively the catalytic activity per amount of enzyme under defined reaction conditions.

As used herein, the term percent "identical," "percent identity," and "percent sequence identity" are defined as amount of identity between a reference amino acid or nucleic acid sequence and at least one other amino acid or nucleic acid sequence. Percent sequence identity can be determined by comparing two optimally aligned sequences, wherein the portion of the sequence being compared may include additions or deletions (i.e., gaps) as compared to the reference sequence (e.g., a nucleic acid or amino acid sequence of the disclosure), which does not include additions or deletions, for optimal alignment of the two sequences. The percentage is calculated by determining the number of positions at which the identical nucleic acid or amino acid residue occurs in both sequences to yield the number of matched positions, dividing the number of matched positions by the total number of positions being compared and multiplying the result by 100 to yield the percentage of sequence identity. Two sequences have percent identity if two sequences have a specified percentage of amino acid residues or nucleic acids that are the same (i.e., 75% identical over a specified region, or, when not specified, over the entire sequence), when compared and aligned for maximum correspondence or designated region as measured using one of the following sequence comparison algorithms or by manual alignment and visual inspection.

One example of an algorithm that is suitable for determining percent sequence identity is the BLAST algorithm, which is described in Altschul et al. (1997) *Nuc. Acids Res.* 25:3389-3402. Software for performing BLAST analyses is publicly available through the National Center for Biotechnology Information. The BLASTP program is used with default settings of a wordlength of 3, and expectation (E) of 10, and the BLOSUM62 scoring matrix (see Henikoff and Henikoff (1992) *Proc. Natl. Acad. Sci. USA* 89:10915) alignments (B) of 50, expectation (E) of 10, M=5, N=−4, and a comparison of both strands. For nucleic acid sequences, the BLASTN program (used for nucleic acid sequences) uses as defaults a wordlength (W) of 11, an expectation (E) or 10, M=5, N=−4 and a comparison of both strands.

DETAILED DESCRIPTION

The following description sets forth numerous exemplary configurations, parameters, and the like. It should be recognized, however, that such description is not intended as a limitation on the scope of the present invention, but is instead provided as a description of exemplary embodiments.

Polypeptides

The present disclosure relates to isolated polypeptides, variants thereof or fragments thereof, having a conserved GPRH (SEQ ID NO: 9) and/or a DPTGxF/Y (SEQ ID NO: 10) motif(s) wherein said polypeptides have lactonase activity. In some embodiments, the polypeptide is an extracellular aldonolactonase. In some preferred embodiments, the polypeptide is an extracellular aldonolactonase containing the amino acid sequence of SEQ ID NO: 1, or a variant thereof having from one to 60 mutations while retaining wild type *S. thermophile* extracellular aldonolactonase 1 activity (e.g., H177 and R302 of SEQ ID NO: 1). In other preferred embodiments, the polypeptide is an extracellular aldonolactonase containing the amino acid sequence of SEQ ID NO: 2, or a variant thereof having from one to 60 mutations while retaining wild type *S. thermophile* extracellular aldonolactonase 2 activity. In some preferred embodiments, the polypeptide is an extracellular aldonolactonase containing the amino acid sequence of SEQ ID NO: 3, or a variant thereof having from one to 60 mutations while retaining wild type *N. crassa* lactonase 2 activity. In some embodiments, the aldonolactonase has a sequence identity of at least 50%, at least 55%, at least 60%, at least 65%, at least 70%, at least 75%, preferably at least 80%, preferably at least 85%, preferably at least 90%, preferably at least 95%, preferably at least 99% or 100% to SEQ ID NO: 1. In other embodiments, the aldonolactonase has a sequence identity of at least 50%, at least 55%, at least 60%, at least 65%, at least 70%, at least 75%, preferably at least 80%, preferably at least 85%, preferably at least 90%, preferably at least 95%, preferably at least 99% or 100% to SEQ ID NO: 2. In some embodiments, the aldonolactonase has a sequence identity of at least 50%, at least 55%, at least 60%, at least 65%, at least 70%, at least 75%, preferably at least 80%, preferably at least 85%, preferably at least 90%, preferably at least 95%, preferably at least 99% or 100% to SEQ ID NO: 3.

In other embodiments, the extracellular aldonolactonase polypeptides include an amino acid sequence that differs from the amino acid sequence of SEQ ID NO: 1 by an insertion or a deletion of one or more amino acid residues and/or the substitution of one or more amino acid residues by different amino acid residues. In other embodiments, the extracellular aldonolactonase polypeptides include an amino acid sequence that differs from the amino acid sequence of SEQ ID NO: 2 by an insertion or a deletion of one or more amino acid residues and/or the substitution of one or more amino acid residues by different amino acid residues. In other embodiments, the extracellular aldonolactonase polypeptides include an amino acid sequence that differs from the amino acid sequence of SEQ ID NO: 3 by an insertion or a deletion of one or more amino acid residues and/or the substitution of one or more amino acid residues by different amino acid residues. In some preferred embodiments, amino acid changes are conservative amino acid substitutions that do not significantly affect the folding and/or activity of the polypeptide; or small deletions, typically of one to about 30 amino acids. Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art. For example, the most commonly occurring substitutions are Ala to Ser, Val to Ile, Asp to Glu, Thr to Ser, Ala to Gly, Ala to Thr, Ser to Asn, Ala to Val, Ser to Gly, Tyr to Phe, Ala to Pro, Lys to Arg, Asp to Asn, Leu to Be, Leu to Val, Ala to Glu, and Asp to Gly as well as the reverse substitutions.

In some embodiments, the extracellular aldonolactonase polypeptides are produced recombinantly, while in others the extracellular aldonolactonase polypeptides are produced synthetically, or are purified from a native source (e.g. *S. thermophile*).

In other embodiments, the extracellular aldonolactonase amino acid sequences and derivatives are produced as N- and/or C-terminal fusion proteins, for example to aid in extraction, detection and/or purification and/or to add functional properties to the extracellular aldonolactonase. Examples of fusion protein partners include, but are not limited to, glutathione-S-transferase (GST), 6×His, GAL4 (DNA binding and/or transcriptional activation domains), FLAG-, MYC-tags or other tags well known to anyone skilled in the art. In some embodiments, a proteolytic cleavage site is provided between the fusion protein partner and the protein sequence of interest to allow removal of fusion protein sequences. Preferably, the fusion protein does not hinder the activity of the extracellular aldonolactonase.

In some embodiments, the extracellular aldonolactonase is fused to a functional domain including a leader peptide, propeptide, binding domain and/or catalytic domain. Suitable binding domains include, but are not limited to, carbohydrate-binding domains (e.g., CBM) of various specificities, providing increased affinity to carbohydrate components present during the application of the extracellular aldonolactonase. Suitable enzymatically active domains possess an activity that supports the action of the extracellular aldonolactonase in producing the desired product. Non-limiting examples of catalytic domains include: cellulases, hemicellulases such as xylanase, endo-mannanases, exo-mannanases, glucanases, arabinases, galactosidases, pectinases, and/or other activities such as proteases, lipases, acid phosphatases and/or others or functional fragments thereof. Fusion proteins are optionally linked to the aldonolactonase through a linker sequence that simply joins the extracellular aldonolactonase and the fusion domain without significantly affecting the properties of either component, or the linker optionally has a functional importance for the intended application.

Alternatively, the extracellular aldonolactonases described herein are used in conjunction with one or more additional proteins of interest. Non-limiting examples of proteins of interest include: hemicellulases, alpha-galactosidases, beta-galactosidases, lactases, beta-glucanases, endo-beta-1,4-glucanases, cellulases, xylosidases, xylanases, xyloglucanases, xylan acetyl-esterases, galactanases, endo-mannanases, exo-mannanases, pectinases, pectin lyases, pectinesterases, polygalacturonases, arabinases, rhamnogalacturonases, laccases, reductases, oxidases, phenoloxidases, ligninases, proteases, amylases, phosphatases, lipolytic enzymes, cutinases and/or other enzymes.

Vectors and Host Cells

In order to produce a fungal extracellular aldonolactonase, the DNA encoding the enzyme can be chemically synthesized from published sequences or obtained directly from host cells harboring the gene (e.g., by cDNA library screening or PCR amplification). In some embodiments, the extracellular aldonolactonase polynucleotide is included in an expression cassette and/or cloned into a suitable expression vector by standard molecular cloning techniques. Such expression cassettes or vectors contain sequences that assist initiation and termination of transcription (e.g., promoters and terminators), and generally contain a selectable marker.

The expression cassette or vector is introduced in a suitable expression host cell, which then expresses the corresponding extracellular aldonolactonase polynucleotide. Particularly suitable expression hosts are bacterial expression host genera including *Escherichia* (e.g., *Escherichia coli*), *Pseudomonas* (e.g., *P. fluorescens* or *P. stutzeri*), *Proteus* (e.g., *Proteus mirabilis*), *Ralstonia* (e.g., *Ralstonia eutropha*), *Streptomyces*, *Staphylococcus* (e.g., *S. carnosus*), *Lactococcus* (e.g., *L. lactis*), or *Bacillus* (*subtilis*, *megaterium*, *licheniformis*, etc.). Also particularly suitable are yeast expression hosts such as *Saccharomyces cerevisiae*, *Schizosaccharomyces pombe*, *Yarrowia lipolytica*, *Hansenula polymorpha*, *Kluyveromyces lactis* or *Pichia pastoris*. Especially suited are fungal expression hosts such as *Aspergillus niger*, *Chrysosporium lucknowense*, *Aspergillus* (e.g., *A. oryzae*, *A. niger*, *A. nidulans*, etc.) or *Trichoderma reesei*. Also suited are mammalian expression hosts such as mouse (e.g., NS0), Chinese Hamster Ovary (CHO) or Baby Hamster Kidney (BHK) cell lines. Other eukaryotic hosts such as insect cells or viral expression systems (e.g., bacteriophages such as M13, T7 phage or Lambda, or viruses such as Baculovirus) are also suitable for producing the extracellular aldonolactonases.

Promoters and/or signal sequences associated with secreted proteins in a particular host of interest are candidates for use in the heterologous production and secretion of extracellular aldonolactonases in that host or in other hosts. As an example, in filamentous fungal systems, the promoters that drive the genes for cellobiohydrolase I (cbh1), glucoamylase A (glaA), TAKA-amylase (amyA), xylanase (ex1A), the gpd-promoter cbh1, cbhII, endoglucanase genes EGI-EGV, Ce161B, Ce174A, eg11-eg15, gpd promoter, Pgk1, pki1, EF-1alpha, tef1, cDNA1 and hex1 are particularly suitable and can be derived from a number of different organisms (e.g., *A. niger*, *T. reesei*, *A. oryzae*, *A. awamori*, and *A. nidulans*). In some embodiments, the extracellular aldonolactonase polynucleotide is recombinantly associated with a polynucleotide encoding a suitable homologous or heterologous signal sequence that leads to secretion of the extracellular aldonolactonase enzyme into the extracellular (or periplasmic) space, thereby allowing direct detection of enzyme activity in the cell supernatant (or periplasmic space or lysate). Particularly suitable signal sequences for *Escherichia coli*, other Gram negative bacteria and other organisms known in the art include those that drive expression of the HlyA, DsbA, Pbp, PhoA, PelB, OmpA, OmpT or M13 phage Gill genes. For *Bacillus subtilis*, Gram-positive organisms and other organisms known in the art, particularly suitable signal sequences further include those that drive expression of the AprE, NprB, Mpr, AmyA, AmyE, Blac, SacB, and for *S. cerevisiae* or other yeast, include the killer toxin, Bart, Suc2, Mating factor α, Inu1A or Ggp1p signal sequence. Signal sequences can be cleaved by a number of signal peptidases, thus removing them from the rest of the expressed protein. In some embodiments, the rest of the extracellular aldonolactonase is expressed alone or as a fusion with other peptides, tags or proteins located at the N- or C-terminus (e.g., 6×His, HA or FLAG tags). Suitable fusions include tags, peptides or proteins that facilitate affinity purification or detection (e.g., 6×His, HA, chitin binding protein, thioredoxin or FLAG tags), as well as those that facilitate expression, secretion or processing of the target endo-β-mannanase. Suitable processing sites include enterokinase, STE13, Kex2 or other protease cleavage sites for cleavage in vivo or in vitro.

Extracellular aldonolactonase polynucleotides are introduced into expression host cells by a number of transformation methods including, but not limited to, electroporation, lipid-assisted transformation or transfection ("lipofection"), chemically mediated transfection (e.g., using calcium chloride and/or calcium phosphate), lithium acetate-mediated transformation (e.g., of host-cell protoplasts), biolistic "gene gun" transformation, PEG-mediated transformation (e.g., of host-cell protoplasts), protoplast fusion (e.g., using bacterial or eukaryotic protoplasts), liposome-mediated transformation, *Agrobacterium tumefaciens*, adenovirus or other viral or phage transformation or transduction.

Alternatively, the extracellular aldonolactonases are expressed intracellularly. Optionally, after intracellular expression of the enzyme variants, or secretion into the periplasmic space using signal sequences such as those mentioned above, a permeabilisation or lysis step can be used to release the extracellular aldonolactonase into the supernatant. The disruption of the membrane barrier is effected by the use of mechanical means such as ultrasonic waves, pressure treatment (French press), cavitation or the use of membrane-digesting enzymes such as lysozyme or enzyme mixtures. As a further alternative, the polynucleotides encoding the extracellular aldonolactonase are expressed by use of a suitable cell-free expression system. In cell-free systems, the polynucleotide of interest is typically transcribed with the assistance of a promoter, but ligation to form a circular expression vector is optional. In other embodiments, RNA is exogenously added or generated without transcription and translated in cell free systems.

Degradation of Biomass to Mono- and Oligosaccharides

The extracellular aldonolactonases and host cells of the present disclosure find use in a variety of industrial applications. For instance the extracellular aldonolactonases disclosed herein find use in biofuel production, food processing, textile cleaning and paper pulp bleaching.

Biofuel Production

The extracellular aldonolactonases of the present disclosure find use in the production of monosaccharides, disaccharides, and oligosaccharides as chemical or fermentation feedstocks from biomass for the production of ethanol, butanol, other products, or intermediates. The extracellular aldonolactonases may be in the form of a crude fermentation broth with or without the cells removed or in the form of a semi-purified or purified enzyme preparation. Alternatively, a host cell of the present disclosure is used as a source of the variant in a fermentation process with the biomass.

Biomass can include, but is not limited to, plant material, municipal solid waste, and wastepaper. Plant material includes but is not limited to miscanthus, switchgrass, cord grass, rye grass, reed canary grass, common reed, wheat straw, barley straw, canola straw, oat straw, corn stover, soybean stover, oat hulls, oat spelt, sorghum, rice hulls, sugarcane bagasse, corn fiber, barley, oats, flax, wheat, linseed, citrus pulp, cottonseed, groundnut, rapeseed, sunflower, peas, lupines, palm kernel, coconut, konjac, locust bean gum, gum guar, soy beans, Distillers Dried Grains with Solubles (DDGS), Blue Stem, corncobs, pine, conifer softwood, eucalyptus, birchwood, willow, aspen, poplar wood, hybrid poplar, energy cane, short-rotation woody crop, crop residue, yard waste, or a combination thereof. The predominant polysaccharide in the primary cell wall of biomass is cellulose, the second most abundant is hemicellulose, and the third is pectin. The predominant polysaccharide in the primary cell wall of biomass is cellulose, the second most abundant is hemicellulose, and the third is pectin. The secondary cell wall, produced after the cell has stopped growing, also contains polysaccharides and is strengthened through polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which helps stabilize the cell wall matrix.

Ethanol is produced by enzymatic degradation of biomass and conversion of the released saccharides to ethanol. This kind of ethanol is often referred to as bioethanol or biofuel. It is used as a fuel additive or extender in blends of from less than 1% and up to 100% (a fuel substitute). Accordingly the extracellular aldonolactonases of the present disclosure find use in the degradation of hexose-lactone intermediates in the degradation of lignocellulosic biomass to aid in the liberation of hexose monosaccharides from biomass. The hexose monosaccharides in turn are used in the production of ethanol. In particular, the extracellular aldonolactonases of the present disclosure are placed in contact with lignocellulosic biomass for the production of hexose aldonic acids such as hexonic acid, hexabioic acid, hexatrionic acid, hexatetraonic acid, hexapentaonic acid, and/or hexahexonic acid. In a further preferred embodiment, the extracellular aldonolactonase is used in combination with other carbohydrases (e.g., glucanase, xylanase, alpha-galactosidase and/or cellulase) for more extensive hydrolysis of the plant material.

Food Processing

Several anti-nutritional factors limit the use of specific plant material in the preparation of animal feed and food for humans. Plant material containing lignocellulosic material such as cellulose greatly reduces the digestibility of the plant material by the animals. The negative effects of cellulose are in particular due to beta-(1, 4) glycosidic bonds that prevent many animals from degrading cellulose to glucose. These effects are reduced through the use of cellulosic degrading enzymes, namely extracellular aldonolactonase enzymes, which permit a higher proportion of plant material to be converted to feed, resulting in a reduction of feed costs. Additionally, through the activity of the extracellular aldonolactonases, cellulosic material is broken down to simpler sugars, which can be more readily assimilated to provide additional energy. Accordingly, compositions containing the extracellular aldonolactonases of the present disclosure are preferably used for processing and/or manufacturing of food or animal feed.

The extracellular aldonolactonases of the present disclosure are useful as additives to feed for mono-gastric animals such as poultry and swine, as well as for human food. In some embodiments, the extracellular aldonolactonases are used to pre-treat the feed instead of as a feed additive. In some preferred embodiment, the extracellular aldonolactonases are added to or used to pre-treat feed from plant material such as rye, sorghum, rice, sugarcane bagasse, corn, barley, oats, flax, wheat, linseed, citrus pulp, cottonseed, groundnut, rapeseed, sunflower, peas, lupines, palm kernel, coconut, konjac, locust bean gum, gum guar, or soy beans.

In compositions containing the extracellular aldonolactonases intended for food processing or as a feed supplement, the compositions optionally contain other substituents such as coloring agents, aroma compounds, stabilizers, vitamins, minerals, other feed or food enhancing enzymes and the like. This applies in particular to the so-called pre-mixes. Food additives according to this present invention may be combined with other food components to produce processed food products. The resulting, combined food additive is mixed in an appropriate amount with other food components such as cereal or plant proteins to form a processed food product.

Textile Cleaning

The extracellular aldonolactonases of the present disclosure find use in detergent compositions to facilitate the removal of lactone-containing stains/soils. In a preferred embodiment the extracellular aldonolactonases s are used in detergent compositions in combination with other enzymes from the group of amylases, cellulases, lipases, pectinases, proteases, and endoglucanases.

Detergent compositions of the present disclosure containing the extracellular aldonolactonases are in any convenient form (e.g., a bar, a tablet, a powder, a granule, a paste or a liquid). A liquid detergent is generally aqueous, typically containing up to 70% water and 0-30% organic solvent(s), or non-aqueous component(s).

The detergent composition contains one or more surfactants (e.g., non-ionic including semi-polar, anionic, cationic and/or zwitterionic). The surfactants are typically present at a level of from 0.1% to 60% by weight. When included, detergents typically contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, or soap. When included, detergents typically contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine (glucamides).

Detergent compositions optionally include 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic add, soluble silicates, or layered silicates. Detergent compositions optionally include one or more polymers such as carboxymethylcellulose (CMC), poly (vinylpyrrolidone), poly (ethylene glycol), poly (vinyl alcohol), poly (vinylpyridine-N-oxide), poly (vinylimidazole), polycarboxylates such as polyacrylates, maleic/acrylic acid copolymers, and lauryl methacrylate/acrylic acid copolymers. The detergent optionally includes a bleaching system (e.g., hydrogen peroxide source) such as perborate or percarbonate, which may be combined with a peracid-forming bleach activator such as tetraacetylethylenediamine or nonanoyloxybenzenesulfonate. Alternatively, the bleaching system contains peroxyacids of the amide, imide, or sulfone type.

In detergent compositions, the extracellular aldonolactonases are added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

Paper Pulp Bleaching

The extracellular aldonolactonases of the present disclosure find use in the enzyme aided bleaching of paper pulps such as chemical pulps, semi-chemical pulps, kraft pulps, mechanical pulps, or pulps prepared by the sulfite method. In some embodiments, the pulps are chlorine free pulps bleached with oxygen, ozone, peroxide or peroxyacids. In some embodiments, the extracellular aldonolactonases are used in enzyme aided bleaching of pulps produced by modified or continuous pulping methods that exhibit low lignin contents. In some embodiments, the extracellular aldonolactonases are applied alone or preferably in combination with xylanase and/or endoglucanase and/or alpha-galactosidase and/or cellobiohydrolase enzymes.

Discussion

Sporotrichum thermophile is a thermophilic fungus isolated from soil and self-heating compost (3). It was demonstrated that S. thermophile very rapidly degrades cellulose. During development of the present disclosure, an enzyme involved in the process of cellulose degradation was isolated from S. thermophile. As disclosed herein, an enzyme containing extracellular aldonolactonase activity was purified, identified, and characterized from the thermophilic ascomycete S. thermophile. The S. thermophile aldonolactonase hydrolyzes hexose δ-lactones over a broad range of pH values. It is stable for several days at 50° C. (the growth condition for production of the enzyme). The expression profile and kinetic parameters of the S. thermophile aldonolactonase were determined on different substrates. The results disclosed herein provide insight into how S. thermophile utilizes aldonolactonase in nutrient acquisition, especially from hexose δ-lactones and how this enzyme can be utilized for biofuel production.

Two evolutionarily distinct groups of enzymes have previously been described with 6-phosphogluconolactonase (PGL) activity. PGL activity in eukaryotes and bacteria is catalyzed by enzymes with homology to the E. coli glucosamine-6-phosphate isomerase NagB (11). Recently, the gene responsible for PGL activity was determined in E. coli (13-14). E. coli PGL has no sequence similarity with the NagB-like PGLs, and 13% sequence identity with N. crassa cis-carboxy-muconate-lactonizing enzyme (CMLE), which is an enzyme involved in the β-ketoadipate pathway (32). Homologues of E. coli PGL are ubiquitous throughout bacteria and fungi. In S. thermophile and other ascomycetes, the NagB-like PGL may be responsible for PGL activity in the pentose phosphate pathway, because the NagB-like PGL is predicted to be intracellular and shows approximately 40% sequence identity to human and yeast PGL. Interestingly, in addition to the NagB-like PGL, many ascomycetes have distant homologues of E. coli PGL that are predicted to be extracellular proteins that may have functions unrelated to that of PGL in the pentose phosphate pathway.

As disclosed herein, an S. thermophile gene with low homology to E. coli PGL was identified. The disclosed S. thermophile gene encodes the enzyme aldonolactonase 1 responsible for extracellular aldonolactonase activity in S. thermophile. As described herein, aldonolactonase 1, encoded by the Spoth11109678 gene, is a glycoprotein and has a broad pH optimum that is similar to the pH profile reported for N. crassa CMLE. The aldonolactonase 1 displays high activity with hexose δ-lactone substrates, but no detectable activity with pentose γ-lactones. Notably, there is only a threefold difference in $k_{cat}/K_M$ values for the δ-lactones of glucose, cellobiose, and lactose, indicating that the enzyme is only interacting with the glucose moiety. This is in stark contrast to the substrate specificity of cellobiose dehydrogenase and many cellulases, which often have much higher affinity for cellobiose over glucose (6, 35). Structural studies on N. crassa CMLE and E. coli PGL have shown that the active sites of these enzymes are highly conserved and probably on or near the surface of the protein (31). A surface exposed active site is consistent with kinetic results disclosed herein.

During growth on lignocellulosic biomass, S. thermophile induces the expression of two E. coli PGL-like lactonases (as disclosed herein, aldonolactonase 1 and aldonolactonase 2). A recent genome wide expression profiling study of N. crassa identified NCU07143, a protein with sequence homology to the S. thermophile lactonases (homology to aldonolactonase 1: 24%; homology to aldonolactonase 2: 67%), as being strongly upregulated during growth on lignocellulose and pure cellulose (21) NCU07143 was also detected in the secretome of N. crassa while growing on cellulose and lignocellulose, confirming that it is also an extracellular enzyme. S. thermophile aldonolactonase 2 has approximately 28% sequence identity with S. thermophile aldonolactonase 1. Despite the low sequence identity, all of the predicted active site residues are conserved in both S. thermophile lactonases and are more closely related to one another than to any other predicted bacterial lactonases.

Genes with sequence similarity to the N. crassa and S. thermophile lactonases are also present in Aspergillus niger and Trichoderma reesei (16). While generally absent in yeast, extracellular aldonolactonase-like genes are widespread in filamentous ascomycetes. All sequenced cellulolytic ascomycetes have genes with homology to either S. thermophile aldonolactonase 1 or aldonolactonase 2. However, BLAST queries against the genomes of currently sequenced basidiomycetes only return proteins with very low homology, and none are predicted to be extracellular proteins.

A periplasmic gluconolactonase (PpgL) with low sequence homology to the S. thermophile lactonases was recently characterized in the bacterium Pseudomonas aeruginosa (33). Similar to fungi, P. aeruginosa contains a NagB-like intracellular PGL that provides aldonolactonase activity in the pentose phosphate pathway (12). Furthermore, it was shown that deletion of PpgL caused severe growth phenotypes on gluconate, 2-ketogluconate, and mannitol, as well as a decrease in pigment formation. However, P. aeruginosa is not cellulolytic, so the PpgL is not involved in any cell wall degradation processes, highlighting the diverse role of lactonases in metabolism.

In short, the biochemical characterization of S. thermophile aldonolactonase 1 described herein, provides guidance as to the use of S. thermophile aldonolactonase 1 in hydrolyzing hexose δ-lactones as a step in the process of degrading lignocellulosic biomass for subsequent biofuel production. Knowledge of the mechanism of action is not necessary in order to make and use the present disclosure.

Example 1

Materials and Methods

Materials. With the exception of the sugar lactones, all chemicals were of reagent grade quality and purchased from commercial vendors. The sugar lactones were synthesized by a modified Frush and Isbell procedure (18). Briefly, in 100 mL of ice-cold water, 0.015 mole of sugar, 0.03 mole of calcium carbonate, and 0.02 mole of bromine were mixed and stored in the dark for 24 hours at room temperature. Residual bromine was removed by purging the solution with nitrogen gas for 1 hour. Excess silver carbonate was then added to the solution and the precipitate removed by filtration. The sugar lactone-containing filtrate was then applied to an amberlite IR-120(H+) resin. The column was washed with 5 column volumes of water and the sugar lactone-containing eluate was collected. The eluate was then concentrated on a rotary evaporator at 55° C. Purity of each sugar lactone was analyzed by high-performance liquid chromatography (HPLC) as described below.

Cloning and Purification of Recombinant *N. crassa* NCU07143 and *S. thermophile* Aldonolactonase 1.

The following primer pairs were used for amplification of NCU07143 and Spoth11109678:

```
NCU07143 Restriction Enzymes: KpnI and XbaI
NCU07143-forward:
                                        (SEQ ID NO: 11)
ATATATATGGTACCGCCACTTTGCTGGTTTCC NCU07143-reverse:
                                        (SEQ ID NO: 12)
ATATATATTCTAGATTCTCTACCCAAACGACAGCACTAAG Spoth1|109678 Restriction Enzymes: KpnI and XbaI
Spoth1|109678-forward:
                                        (SEQ ID NO: 13)
ATATATATGGTACCGCCCCGGTCTGTGGC Spoth1|109678-reverse:
                                        (SEQ ID NO: 14)
ATATATATTCTAGATTCTGCTTAAACGTGGCAAAGTTG
```

For Spoth11109678, cDNA was isolated from *S. thermophile* cultures grown on Vogel's minimal media supplemented with 2% (w/v) cotton balls.

For NCU07143, cDNA was isolated from *N. crassa* cultures grown on Vogel's minimal media supplemented with 2% (w/v) Avicel.

The PCR products were gel purified and cloned into Zero Blunt® TOPO® vectors according to the manufacturer's instructions. The Ppiczα-A vector and the TOPO vector containing the lactonases were digested with KpnI and XbaI. The inserts and cut vectors were gel purified. The vector was then treated with antarctic phosphatase. The insert was ligated into the Ppiczα-A vector using T4 DNA ligase. The plasmid with the correct insert was then transformed into *Pichia pastoris* according to the manufacturer's instructions (Pichia EasySelect Expression Kit, Invitrogen, Carlsbad, Calif.). Expression was induced using methanol at a concentration of 0.5% (v/v) according to the *Pichia* EasySelect Expression Kit's instructions.

Figure 5:
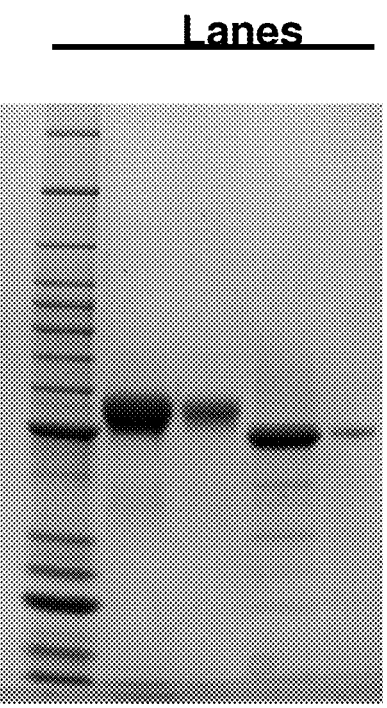
FIG. 5 depicts the results of SDS-PAGE analyses of purified recombinant Spoth11109678 and NCU07143 using a 4-15% Criterion (Biorad) gel. Lane1: Benchmark Protein ladder (dark bands at 50 kDa and 20 kDa), Lane2: Spoth11109678 expressed in *Pichia*, Lane3: Spoth11109678 expressed in *Pichia* (5× diluted), Lane4: NCU07143 expressed in *Pichia*, Lane5: NCU07143 expressed in *Pichia* (5× diluted). The apparent molecular mass of Spoth11109678 and NCU07143 were between 50-60 kDa and approximately 49 kDa, respectively.

After 2 days of induction with methanol, cultures were harvested. Cells were removed by centrifugation and the culture broth was concentrated and buffer exchanged using tangential flow filtration into 25 mM Tris pH 8.0. The concentrated culture supernatant was then run over a 5 mL Fastflow HisTrap column (GE Healthcare, Piscataway, N.J.). Recombinant protein was eluted from the column with 200 mM imidazole in 25 mM Tris pH 8.0 and 500 mM NaCl. SDS-PAGE analyses of the purified proteins are shown in FIG. 5.

Cloning and Expression of Recombinant *S. thermophile* Aldonolactonase 2 (Spoth1189286).

*S. thermophile* was grown on Vogel's media supplemented with 2% w/v glucose for 30 hours at 48° C. Mycelia was then isolated by filtration, frozen in liquid nitrogen and ground to a fine powder using a mortar and pestle. Approximately 100 mg of the powder was processed using a Qiagen Plant DNEasy genomic DNA isolation kit according to the manufacturer's instructions. Spoth1189286 was amplified from the genomic DNA using the following primers: Spoth1189286-Forward (TACTTCCAATCCAATGCAATGT (SEQ ID NO: 15)) and Spoth1189286-Reverse (CTCCCACTACCAATGCCCTGC (SEQ ID NO: 16)).

The PCR product was gel purified and treated with T4 DNA polymerase in the presence of 25 mM dCTP to generate sticky ends. The pNeurA plasmid was digested with SspI and gel-purified. The plasmid was then treated with T4 DNA polymerase in the presence of 25 mM dGTP to generate sticky ends. The pNeurA plasmid and the Spoth1189286 PCR products with sticky ends were then mixed together and allowed to anneal at 22° C. for 5 minutes followed by transformation into chemically competent *E. coli*. Several clones were sequenced to confirm the correct insertion of Spoth1189286 into pNeurA. pNeurA containing Spoth1189286 was transformed into a histidine auxotroph of *Neurospora crassa* as previously described (19). Transformants able to grow on media lacking histidine were then screened for GFP fluorescence to confirm the production of Spoth1189286. Once a transformant was isolated with GFP, the conidia were inoculated onto a fresh slant containing Vogel's media agar supplemented with 2% w/v sucrose. The culture was grown on slants for 10 days and then inoculated into liquid culture containing Vogel's media supplemented with 2% w/v sucrose. After 2 days of growth in liquid culture, the mycelia was washed with water and transferred to Vogel's media supplemented with 2% w/v sodium acetate to induce expression of Spoth1189286. After 2 days of growth on the acetate media, the culture was harvested, filtered over 0.2 micron PES filters to remove any residual biomass, and concentrated using a tangential flow filtration system with a 10,000 MWCO PES membrane.

Lactonase activity on gluconolactone was confirmed using the standard gluconolactonase assay (as described in other sections). The protein was not further purified because the affinity purification tag was removed by endogenous proteases in *N. crassa*.

Strains and Growth Conditions to Purify Endogenous *S. thermophile* Aldonolactonase 1.

*S. thermophile* ATCC strain 42464 was obtained from the American Type Culture Collection. *S. thermophile* was maintained on Vogel's salts agar (20) containing 2% cellobiose. Conidia (fungal spores) were isolated from agar plates grown for 7 days at 48° C. For aldonolactonase induction studies fresh *S. thermophile* conidia were inoculated into liquid culture containing Vogel's salts supplemented with either 2% glucose or cellulose, and grown at 48° C. with shaking at 200 rpm.

Endogenous *S. thermophile* Aldonolactonase 1 Purification.

For aldonolactonase purification, *S. thermophile* conidia were inoculated into a complex media containing 1.0 g/L casamino acids, 1.0 g/L yeast extract, 0.5 g/L potassium chloride, 0.2 g/L magnesium sulfate heptahydrate, 1.0 g/L potassium dihydrogen phosphate, and trace elements solution. The culture was grown at 48° C. with shaking at 200 rpm for 24 hours and then the fungal mycelia (vegetative part of fungus) was harvested by filtration and used to inoculate fresh complex media, containing 5 g/L cellulose (Avicel® PH 101, Sigma, St. Louis, Mo.) to induce expression of the aldonolactonase.

After 48 hours of growth on complex media containing cellulose, *S. thermophile* mycelia and residual cellulose were removed from the culture by filtering over 0.2 micron polyethersulfone (PES) filters. The filtered culture broth was then concentrated and buffer exchanged using tangential flow filtration with a 10 kDa molecular weight cut-off (MWCO) PES membrane (Millipore, Billerica, Mass.) into 25 mM 4-(2-hydroxyethyl)-1-piperazineethanesulfonic acid (HEPES) buffer, pH 7.4. The concentrated culture broth was then mixed with excess cellulose to remove cellulose-binding proteins and the cellulose particles were separated by vacuum filtration over a glass microfiber filter. The filtrate was then loaded onto a 5 mL Q Sepharose® High Performance (Q HP) anion exchange chromatography column (GE Healthcare) at a rate of 5 mL/min. Aldonolactonase was then eluted from the Q HP column with a sodium chloride (NaCl) linear concentration gradient ranging from 0 to 0.5 M NaCl over 15 column volumes. Column fractions were then collected and assayed form aldonolactonase activity (see above). Fractions with the highest aldonolactonase activity were pooled and buffer exchanged into 25 mM HEPES buffer pH 7.4. Each protein-containing fraction was then loaded onto a Mono Q™ 10/100 GL high performance anion exchange chromatography column (GE Healthcare) and eluted with a NaCl linear concentration gradient ranging from 0 to 0.5 M NaCl over 8 column volumes. Fractions containing aldonolactonase activity were pooled and adjusted to 1.5 M ammonium sulfate and 25 mM HEPES, pH 7.4. Each sample was then loaded onto a 1.0 mL RESOURCE™ PHE hydrophobic interaction chromatography column (GE Healthcare). Aldonolactonase enzyme does not bind the PHE column and thus flows through as a pure species. The purified aldonolactonase was concentrated and buffer exchanged with 10 kDa MWCO spin concentrators (Millipore) and stored at −80° C. Aldonolactonase activity is stable for several months under these conditions.

Enzyme Assays.

Aldonolactonase activity was measured as described by Hestrin (21). The reactions were carried out in triplicate in 96-well microtiter plates. Briefly, 100 µL of 100 mM freshly dissolved sugar lactone was immediately mixed with 100 µL of 10 nM aldonolactonase enzyme buffered in 100 mM sodium acetate pH 5.0 for 1 minute at 25° C. The reaction was quenched by adding 40 µL of alkaline hydroxylamine (2.0 M hydroxylamine hydrochloride, 1.5 M sodium hydroxide) for 1 minute. Twenty microliters of 4.0 M hydrochloric acid was then added to acidify the solution and stabilize the sugar hydroxamate. Color was developed by adding 20 µL of 0.5 M ferric chloride ($FeCl_3$) and the absorbance at 540 nm was measured. For all experiments, control measurements were made on control samples where no enzyme was added. The background hydrolysis was subtracted from the total hydrolysis in the presence of enzyme. This typically amounted to less than 10% of the total lactone.

Mass Spectrometry Peptide Fingerprinting.

Thirty-six milligrams of urea, 5 µL of 100 mM DTT, and 5 µL of 1.0 M Tris, pH 8.5, were added to a 100 µL aqueous solution of 10 µM aldonolactonase and heated at 70° C. for 1 hour. After heat denaturation, 700 µL of 25 mM ammonium bicarbonate and 140 µL of methanol were added to the solution followed by treatment with 50 µL of 100 µg/mL trypsin in 50 mM sodium acetate, pH 5.0. The protein was digested with trypsin overnight at 37° C. After digestion the volume was reduced using a vacuum concentrator, and washed with purified, de-ionized water three times. Residual salts in the sample were removed by OMIX® microextraction pipette tips according to the manufacturer's instructions (Varian, Palo Alto, Calif.). Peptides from the trypsin digest were analyzed using a tandem mass spectrometer that was connected in-line with ultraperformance liquid chromatography as described (22).

Liquid Chromatography-Mass Spectrometry Analysis of Proteins.

Protein samples were analyzed using a 1200 series liquid chromatograph (LC; Agilent, Santa Clara, Calif.) that was connected in-line with an LTQ Orbitrap XL™ hybrid mass spectrometer equipped with an Ion Max™ electrospray ionization source (ESI; Thermo Fisher Scientific, Waltham, Mass.).

The LC was equipped with a $C_8$ guard (Poroshell 300SB-C8, 5 µm, 12.5×2.1 mm, Agilent), analytical (75×0.5 mm) columns, and a 100 µL sample loop. LC solvent A included 0.1% formic acid/99.9% water (v/v), and solvent B included 0.1% formic acid/99.9% acetonitrile (v/v). Sample solutions contained in auto-sampler vials sealed with rubber septa caps were loaded into the Agilent 1200 auto-sampler compartment prior to analysis. For each sample, approximately 100 picomoles of protein analyte were injected onto the column. Following sample injection, analyte trapping was performed for 5 min with 99.5% of solvent A at a flow rate of 90 µL/min. The elution program included a solvent B linear concentration gradient ranging from 30% to 95% solvent B over 24.5 min, incubation at isocratic conditions at 95% solvent B for 5 min, a solvent B linear concentration gradient to 0.5% solvent B over 0.5 min, and incubation at isocratic conditions at 0.5% solvent B for 9.5 min at a flow rate of 90 µL/min. The column and sample compartments were maintained at 35° C. and 10° C., respectively. Solvent blanks containing only purified, de-ionized water were run between samples, and the auto-sampler injection needle was rinsed with purified, de-ionized water after each sample injection to avoid cross-contamination between samples.

The connections between the LC column exit and the ESI probe of the mass spectrometer were made using PEEK™ tubing (0.005" i.d.×1/16" o.d., Western Analytical, Lake Elsinore, Calif.). External mass calibration was performed prior to analysis using the standard LTQ MS calibration mixture containing caffeine, the peptide MRFA, and the Ultramark 1621® mixture of fluorinated phosphazenes dissolved in 51% acetonitrile/25% methanol/23% water/1% acetic acid solution (v/v). The ESI source parameters were as follows: ion transfer capillary temperature 275° C., normalized sheath gas (nitrogen) flow rate 25%, ESI voltage 2.5 kV, ion transfer capillary voltage 33 V, and tube lens voltage 125 V. Mass spectra were recorded in the positive ion mode over the range m/z=500 to 2000 using the Orbitrap™ mass analyzer, in profile format, with a full MS automatic gain control target setting of $5 \times 10^5$ charges and a resolution setting of $6 \times 10^4$ (at m/z=400, FWHM). Raw mass spectra were processed using the Xcalibur™ software (version 4.1, Thermo), and measured charge state distributions were deconvoluted using the Pro-Mass® software (version 2.5 SR-1, Novatia, Monmouth Junction, N.J.) using default "large protein" parameters and a background subtraction factor of 1.5.

Nanoelectrospray Ionization Mass Spectrometry of Native Proteins.

Mass spectra of native proteins were acquired using a quadrupole time-of-flight (Q-T of) mass spectrometer equipped with a Z-spray® electrospray ionization (ESI) source (Q-T of Premier™, Waters, Milford, Mass.). Ions were formed from aqueous solutions containing 10 µM analyte protein and 10 mM ammonium acetate, using positive-ion nanoelectrospray ionization (nanoESI). NanoESI emitters were made from borosilicate glass capillary tubes (1.0 mm o.d./0.78 mm i.d, Sutter Instruments, Novato, Calif.) that were pulled to a tip with an inner diameter of approximately 5 to 20 µm using a Flaming/Brown micropipette puller (Model P-87, Sutter).

Approximately 10 μL of each sample solution was added into a nanoESI emitter using a 10 μL syringe (Hamilton, Reno, Nev.). The electrospray was initiated by gradually increasing the DC potential applied to a platinum wire (0.127 mm diameter, Aldrich, Milwaukee, Wis.), which was inserted into the nanoESI emitter to within approximately 2 mm of the tip, until the onset of mass spectral signal. No back pressure was used for nanoESI. Instrument parameters during data collection were as follows: nanoESI voltage 1.8 kV, sampling cone voltage 30 V, extraction cone and ion guide voltages both 4.0 V, source block temperature 80° C., accelerating voltage into the argon-filled cell 2 V, ion transfer stage pressure $6 \times 10^{-3}$ mbar, argon-filled cell pressure $8 \times 10^{-3}$ mbar, and T of analyzer pressure $8 \times 10^{-7}$ mbar. The pressure in the first pumping stage was increased to 7.4 mbar by adjusting an Edwards® Speedivalve vacuum valve to favor the preservation of non-covalent complexes in gas phase. No cone gas flow was used. The T of analyzer was operated in "V" mode. External mass calibration of the T of analyzer was performed immediately prior to measurements. Mass spectra were processed using the MassLynx™ software (version 4.1, Waters).

Multiple Sequence Alignments and Phylogenetics.

Orthologues of the S. thermophile aldonolactonase protein were found with a basic local alignment search tool (BLAST; 23) query of the aldonolactonase sequence against a database of predicted fungal proteins from finished and ongoing fungal genome projects. Bacterial sequences were obtained by BLAST against the National Center for Biotechnology Information (NCBI) database. Multiple sequence alignments were done locally using the T-COFFEE multiple sequence alignment software (24). A maximum likelihood phylogeny was determined using the PHYlogenetic Inferences Using Maximum Likelihood (PhyML) software, version 3.0, with 100 bootstraps through the Phylogeny.fr webserver (25).

mRNA-Seq expression profiling. Messenger RNA was isolated from S. thermophile after 20 hours of growth and Illumina® cDNA libraries were generated following standard protocols according to the manufacturer's instructions (26). Sequencing was performed on the Illumina® Genome Analyzer II high-throughput sequencing system. Read lengths were trimmed to 31 nt and mapped against all predicted transcripts in the S. thermophile genome using the MAQ genome short read alignment software (27). Expression was normalized by counting the number of reads mapped per kilobase of exon model divided by the total number of mapped reads in the whole dataset, RPKM (28). Mapping entailed matching the 31-nt mRNA sequences against the predicted full length mRNA sequences determined computationally from the genome sequence. If a gene is highly expressed, there would be many fragments generated by the Solexa sequencing that match the gene sequence. If, in contrast, the gene is expressed at low levels, very few Solexa reads would match the gene sequence.

Results

The gene encoding S. thermophile extracellular aldonolactonase 1 is 1,491 base pairs in length, and contains three introns. The open reading frame is 1,206 base pairs in length and encodes a 401 amino acid polypeptide with a calculated mass of 42,509 Da. The protein is predicted to contain a 20 amino acid N-terminal signal peptide (29). There are also three predicted N-linked glycosylation sites (30). Indeed, no peptides were detected in regions with predicted glycosylation, thud providing evidence of N-linked glycosylation.

Purification and Properties of Recombinant S. thermophile Aldonolactonase 1.

FIG. 5 depicts the SDS-PAGE analysis of the purified protein. Apparent molecular mass of the aldonolactonase was between 50-60 kDa and the recombinant enzyme had similar activity as the endogenously purified protein described below.

Purification and Properties of Endogenous S. thermophile Aldonolactonase 1.

Figure 6:
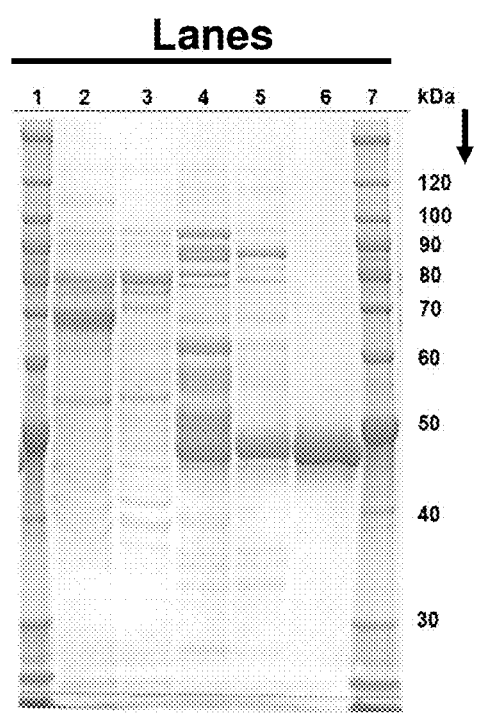
FIG. 6 depicts the results of SDS-PAGE analysis of purification fractions of endogenous *S. thermophile* extracellular aldonolactonase 1. Fractions were denatured by boiling in SDS buffer containing DTT. Lanes 1 and 7 depict protein ladders, lane 2 depicts crude supernatant concentrate, lane 3 depicts supernatant after removal of cellulose binding proteins, lane 4 depicts supernatant after Q HP ion-exchange chromatography, lane 5 depicts supernatant after Mono Q ion-exchange chromatography, and lane 6 depicts supernatant after PHE hydrophobic interaction chromatography.
Figure 7:
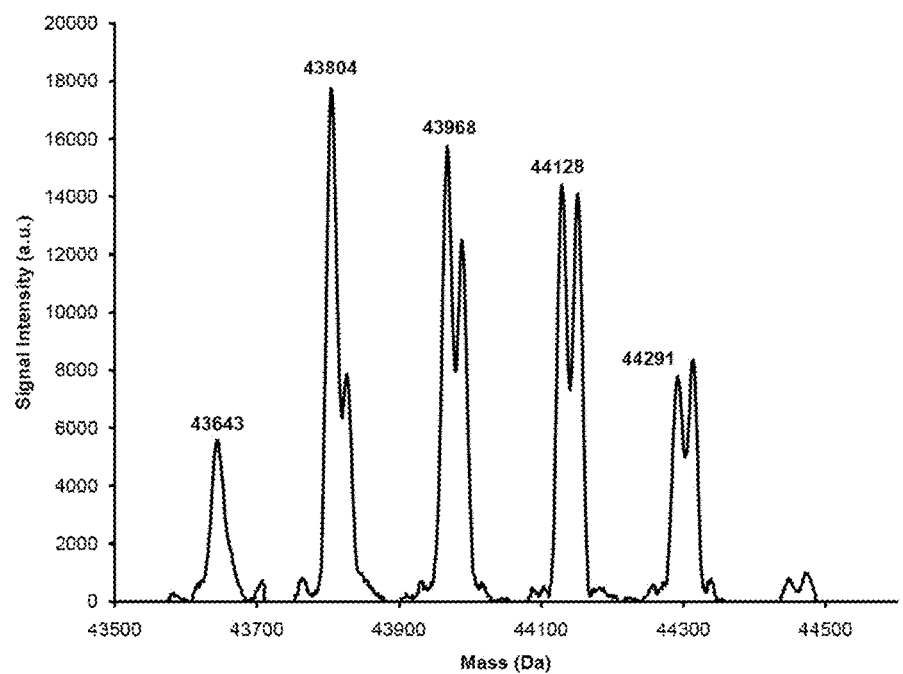
FIG. 7 depicts the results of mass spectrometry. The deconvoluted mass spectrum of purified, intact *S. thermophile* extracellular aldonolactonase shows that the mass difference between glycoforms is approximately 162 daltons. Mass difference for double peaks is approximately 20 daltons.

The S. thermophile aldonolactonase activity was isolated from the culture broth of S. thermophile grown on rich media containing cellulose as the carbon source. Purification of S. thermophile aldonolactonase was performed in five steps (Table 1). The aldonolactonase was purified 25-fold with an overall yield of 25%. Two key purification steps were the Q HP ion-exchange chromatography and the PHE hydrophobic interaction chromatography. SDS-PAGE of the purified aldonolactonase indicated a molecular mass of approximately 48 kDa (FIG. 6). Liquid chromatography-mass spectrometry (LC-MS) analysis of the intact aldonolactonase showed several species centered around 44 kDa and differing in mass by approximately 162 daltons, which corresponds to the mass of a hexose subunit (FIG. 7). This result indicated the presence of protein glycosylation, a common post-translational modification in extracellular proteins secreted by fungi. Native protein LC-MS analysis of the aldonolactonase in 10 mM ammonium acetate indicated the protein is a monomer in solution, which is consistent with gel filtration retention times.

TABLE 1

Purification of endogenous S. thermophile aldonolactonase 1.

| Step | Volume (mL) | Protein (mg) | Total Activity$^\alpha$ (U) | Spec. Act. (U/mg) | Purification (fold) | Recovery (%) |
| --- | --- | --- | --- | --- | --- | --- |
| Crude Concentrate | 175 | 162.1 | 101,140 | 620 | 1 | 100 |
| Cellulose Binding | 120 | 68.2 | 60,060 | 880 | 1.4 | 60 |
| Q HP | 10 | 14.6 | 39,510 | 2,710 | 4.3 | 39 |
| MonoQ | 6 | 3.9 | 24,930 | 6,430 | 10.3 | 25 |
| Resource PHE | 9 | 1.6 | 25,160 | 15,360 | 24.6 | 25 |

$^\alpha$Activity was measured by adding diluted enzyme mixture with 50 mM glucono-δ-lactone and quenching the reaction after 1 minute. One unit of activity is defined as the hydrolysis of 1 μmol of glucono-δ-lactone per minute at 25° C.

The second-order rate constant, $k_{cat}/K_M$, for the *S. thermophile* aldonolactonase 1 with glucono-δ-lactone as a substrate at 25° C. and pH 5.0 was approximately $6 \times 10^5$ M$^{-1}$ s$^{-1}$ (Table 2; FIG. 8*a*). This activity is approximately 20-fold higher than that reported for lactonases isolated from other filamentous fungi (16). The aldonolactonase reaction velocity showed a broad pH optimum (FIG. 9), with only a 3-fold change in activity from pH 3.0 to pH 8.0.

TABLE 2

Steady-state kinetic constants for various aldonolactones.

| Substrate | $K_M$ (mM) | $k_{cat}$ (s$^{-1}$) | $k_{cat}/K_M$ ($10^5$ M$^{-1}$s$^{-1}$) |
| --- | --- | --- | --- |
| D-Glucono-δ-lactone | 20.3 ± 4.1 | 11,700 ± 1000 | 5.8 ± 1.3 |
| D-Cellobiono-δ-lactone | 21.6 ± 1.8 | 29,100 ± 1,100 | 13.5 ± 1.2 |
| D-Lactono-δ-lactone | 5.9 ± 2.4 | 7,400 ± 600 | 12.5 ± 5.2 |

Substrate Specificity of *S. thermophile* Aldonolactonase 1.

Figure 8:
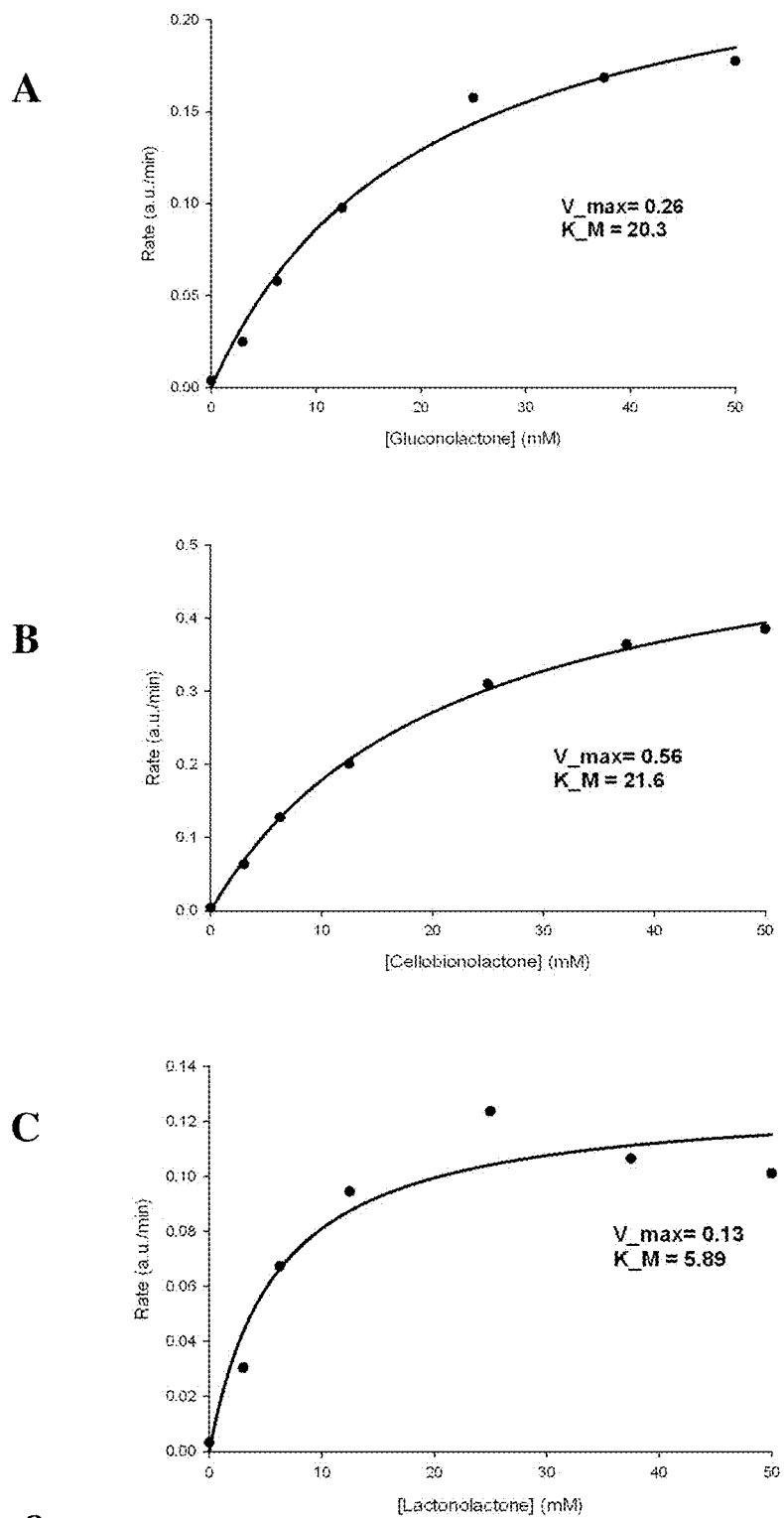
FIG. 8 depicts the results of kinetic assays on *S. thermophile* aldonolactonase 1 using three different hexose-δ-lactones as substrate: (a) glucono-δ-lactone, (b) cellobiono-δ-lactone, and (c) lactono-δ-lactone.
Figure 9:
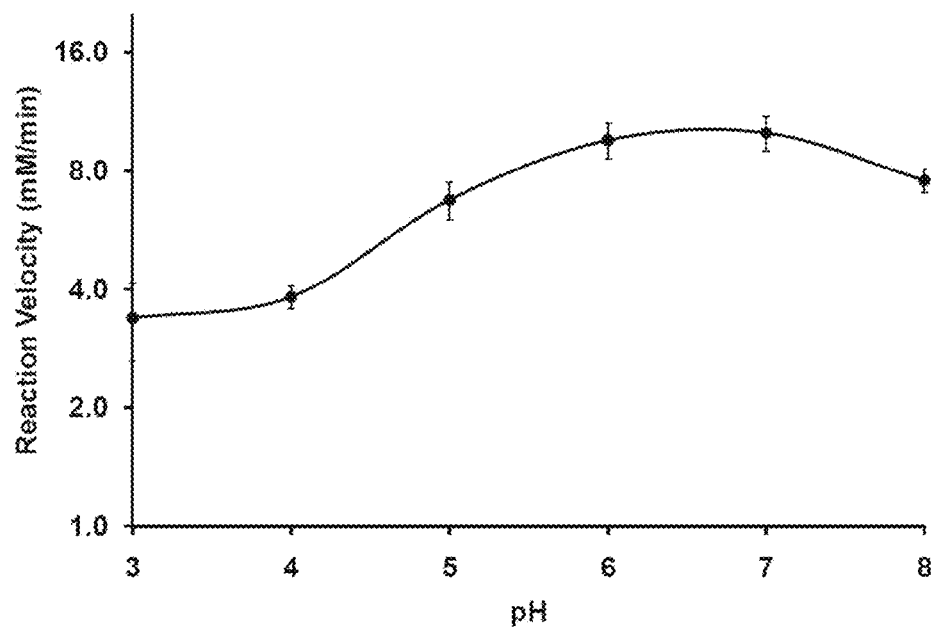
FIG. 9 depicts the pH profile of *S. thermophile* aldonolactonase 1. Reactions were conducted at room temperature for 1 minute with 10 nM aldonolactonase, 50 mM glucono-δ-lactone, and 100 mM buffer. Buffers used included sodium citrate, pH 3.0; sodium acetate, pH 4.0; sodium acetate, pH 5.0; sodium succinate, pH 6.0; HEPES, pH 7.0; and Tris, pH 8.0. Error bars represent the standard deviation of three replicate experiments.

Pentose and hexose sugar lactones were synthesized as described above. The *S. thermophile* aldonolactonase 1 was shown to completely hydrolyze gluconolactone, cellobionolactone, and lactonolactone to their corresponding aldonic acids. The initial rates of hydrolysis were similar for gluconolactone, cellobionolactone, and lactonolactone (Table 2; FIG. 8 *a-c*). The $k_{cat}/K_M$ for the three substrates varied by less than 3 fold, indicating that the reducing-end glucose moiety of each substrate is what principally interacts with the aldonolactonase. Xylonolactone and arabinolactone, which are present as γ-lactones in aqueous solution (7), were not hydrolyzed by the enzyme. Glucono-δ-lactone can be partially converted to glucono-γ-lactone by heating in water above 100° C. When a supersaturated aqueous solution of glucono-δ-lactone was autoclaved for 15 minutes and then provided as a substrate, a portion of the lactone was rapidly hydrolyzed, while the remaining lactone was hydrolyzed at a much slower rate. This result is consistent with rapid, enzyme catalyzed hydrolysis of the δ-lactone ring, and slow, uncatalyzed hydrolysis of the γ-lactone ring.

Amino Acid Sequence of *S. thermophile* Aldonolactonase 1.

The purified aldonolactonase was digested with trypsin and the tryptic peptides were analyzed using LC-MS. A database search against all possible tryptic fragments in the *S. thermophile* proteome (Joint Genome Institute (MI; *Sporotrichum thermophile*, v1.0) revealed seven peptides matching Spoth11109678, and one peptide matching Spoth11103702. The signal intensity for the Spoth11103702 peptide was 20- to 100-fold lower than the signal intensity for peptides from Spoth11109678, indicating that it was a trace impurity of the protein preparation. Based on the number of peptides detected and relative signal intensity for those peptides, the *S. thermophile* aldonolactonase enzyme was identified as Spoth11109678 (*S. thermophile* extracellular aldonolactonase 1).

*S. thermophile* Aldonolactonase Sequence Alignments and Phylogenetic Relationships.

The *S. thermophile* extracellular aldonolactonase 1 amino acid sequence was analyzed for conserved domains using the Pfam protein family database (31). Immediately after the predicted signal peptide is a 370 amino acid domain classified as a 3-carboxy-cis,cis-muconate lactonizing enzyme (CMLE). The overall sequence identity of the *S. thermophile* extracellular aldonolactonase 1 with *Neurospora crassa* cis-carboxy-muconate lactonizing enzyme (32-33) is only 13%. However, all of the predicted active site residues in *N. crassa* CMLE (32) are conserved in the *S. thermophile* extracellular aldonolactonase 1 (FIG. 10).

Predicted homologues of the aldonolactonase were retrieved from NCBI and JGI, based on amino acid sequences showing significant similarity by BLAST. Homologues of the extracellular aldonolactonase are present in many filamentous ascomycetes, and most are predicted to be secreted. Some basidiomycetes have distant homologues, which are not predicted to be secreted. The only characterization of any of these proteins in the literature is in bacteria and most of those have very low sequence identity (<30% sequence identity). The closest biochemically characterized bacterial proteins with homology to the *S. thermophile* extracellular aldonolactonase were shown to have 6-phosphogluconolactonase activity in *Escherichia coli* (13-14) and multifunctional aldonolactonase activity in *Pseudomonas aeruginosa* (33) (FIG. 10). No homologues were found in plants or animals with sequenced genomes.

All of the sequences are predicted to have the same fold and probably the same active site. As mentioned earlier, and as shown in the multiple sequence alignment in FIG. 10, the conserved active site residues of the distantly related *N. crassa* CMLE (e.g., H149 and E213) are present in *S. thermophile* aldonolactonases 1 and 2 (residues marked by solid black dots), despite CMLE and the aldonolactonase 1 sharing only 13% sequence identity. As the legend for FIG. 10 refers to, the symbols indicate proteins that have had some form of characterization done on them. This includes x-ray crystal structures (by structural genomics consortia, filled triangles) or biochemical/genetic characterization (filled squares). Homology models using some of the bacterial homologues as a template indicate that the active site residues are all concentrated on a very solvent exposed region on the surface of the protein.

Figure 10:
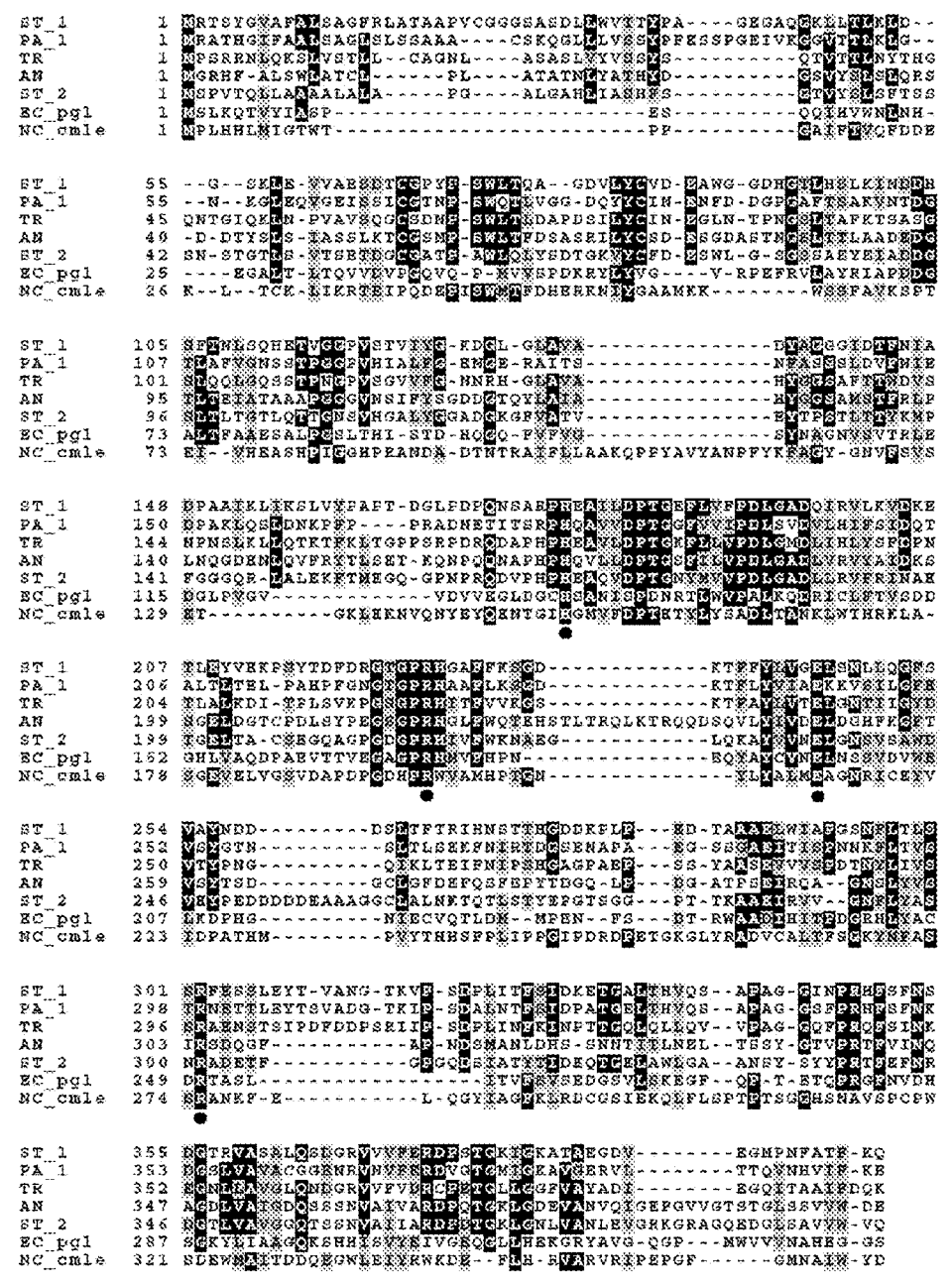

All the predicted bacterial and fungal aldonolactonases seem to have a conserved GPRH motif (SEQ ID NO: 9) (circled in FIG. 10; SEQ ID NO: 1). Only the *N. crassa* CMLE sequence, which is probably not a lactonase (33), does not contain the conserved G and H residues in the motif (FIG. 10). All the fungal lactonases also have a conserved DPT-GxF/Y motif (SEQ ID NO: 10) that is partially absent in *N. crassa* CMLE and mostly absent in *E. coli* Pgl.

Figure 11:
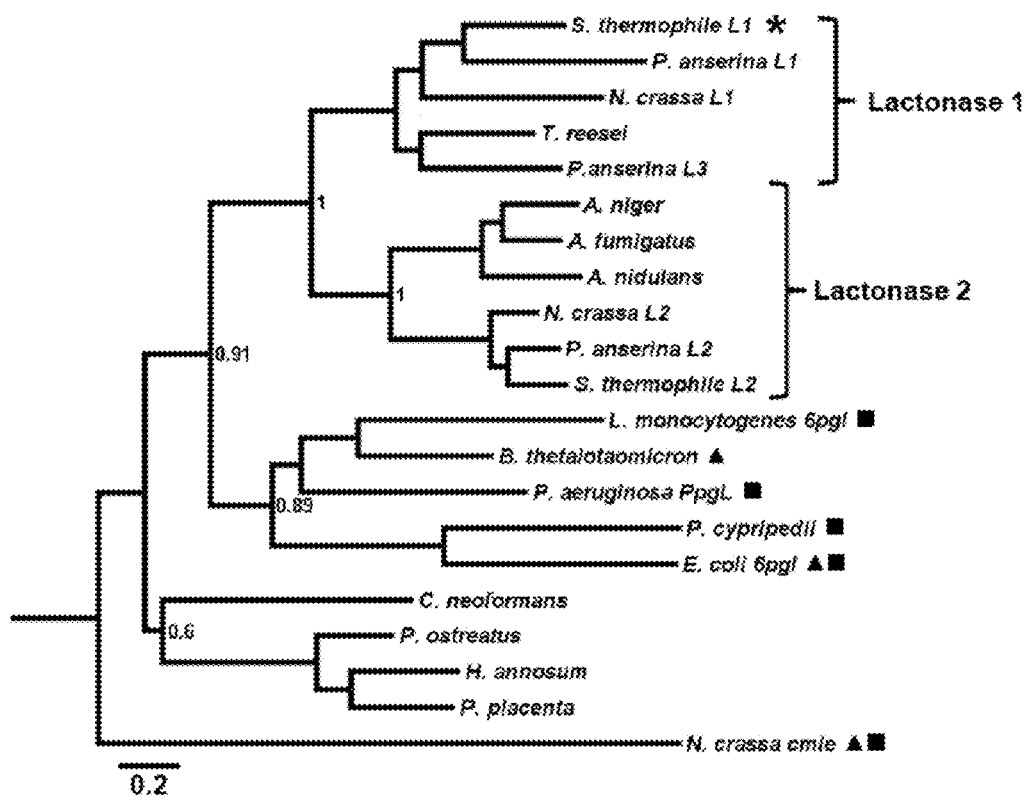
FIG. 11 depicts a phylogenetic tree of representative sequences showing sequence similarity with *S. thermophile* extracellular aldonolactonase 1. Bootstrap values from 100 iterations are listed. (*) depicts *S. thermophile* extracellular aldonolactonase 1, (■) depicts protein that has been characterized biochemically, and (▲) depicts protein for which an x-ray crystal structure has been solved.

A sequence alignment and maximum likelihood phylogeny (PhyML) of representative homologues showed two distinct clades within the ascomycetes (FIG. 11). Many sordariomycetes have two proteins with homology to the *S. thermophile* extracellular aldonolactonase. Group 1 lactonases are less conserved than group 2 lactonases. The aspergilli only possess a single copy of a group 2 aldonolactonase. Expression of the group 2 aldonolactonase in *N. crassa* was shown to be highly upregulated in response to growth on pure cellulose or ground *Miscanthus* stems and was identified in the secretome under both conditions (21).

*S. thermophile* Aldonolactonase Induction by Cellulose.

Figure 12:
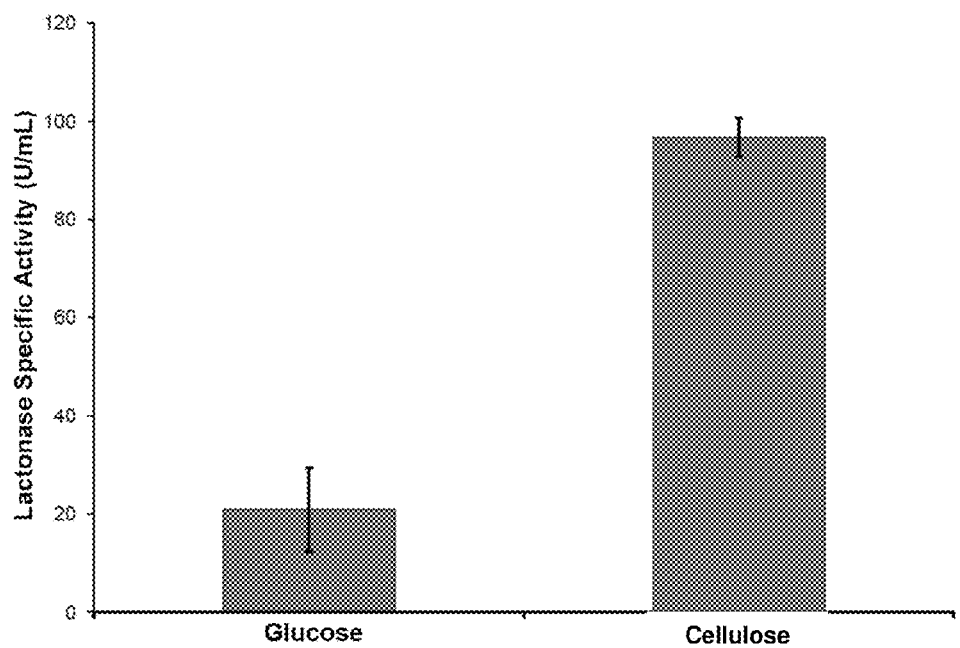
FIG. 12 depicts the specific activity of *S. thermophile* extracellular aldonolactonase 1 in culture broth collected after 4 days of *S. thermophile* growth on Vogel's salts supplemented with 2% glucose or 2% cellulose.

After four days of growth, *S. thermophile* extracellular aldonolactonase activity was approximately 4-fold higher in culture broth of *S. thermophile* grown on cellulose compared to that of culture broth of *S. thermophile* grown on glucose (FIG. 12). This result indicates that *S. thermophile* extracellular aldonolactonase 1 can be used in the process of degrading cello-oligosaccharide-containing biomass.

Figure 13:
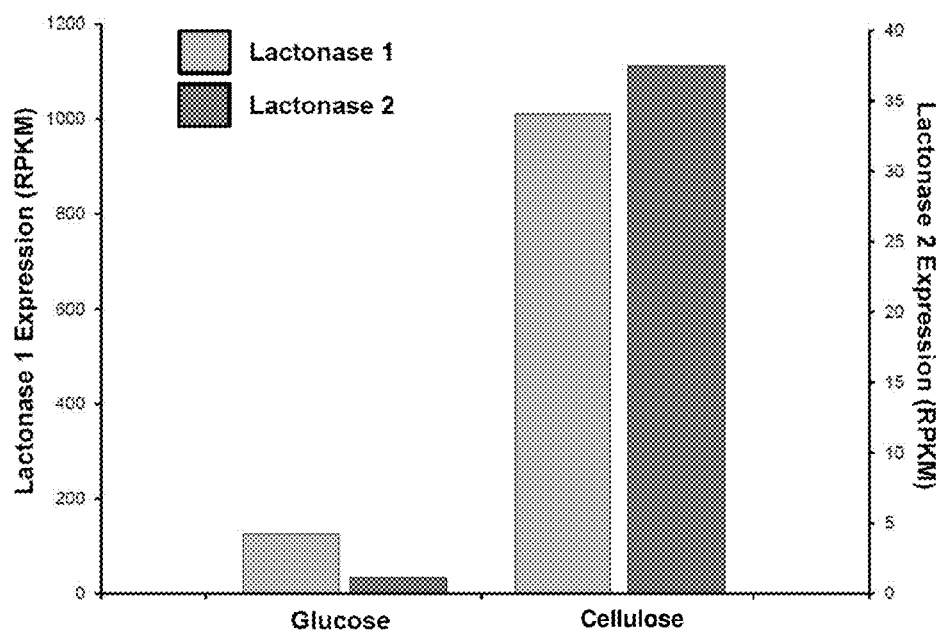
FIG. 13 depicts RNA-Seq expression profiling of *S. thermophile* extracellular aldonolactonase 1 and *S. thermophile* extracellular aldonolactonase 2 after 20 hours of *S. thermophile* growth on glucose or cellulose. Expression is normalized based on the number of mapped reads per kilobase transcript per million mapped reads (RPKM). Aldonolactonase 1 is depicted in light gray and aldonolactonase 2 is depicted in black.

Using the nucleotide sequence of *S. thermophile* extracellular aldonolactonase 1 (Spoth11109678) and *S. thermophile* extracellular aldonolactonase 2 (Spoth1189286), expression levels of the two *S. thermophile* aldonolactonases were investigated using mRNA-Seq (27). The *S. thermophile* extracellular aldonolactonase 1 showed a relatively high basal expression level when grown on glucose, but was upregulated approximately six-fold when grown on cellulose (FIG. 13). The *S. thermophile* extracellular aldonolactonase 2 was expressed at extremely low levels when grown on glucose, and was also strongly induced when grown on cellulose. However, the absolute level of expression was substantially lower for aldonolactonase 2 (approximately 40 RPKM) than for aldonolactonase 1 (approximately 1000 RPKM). These results indicate that *S. thermophile* extracellular aldonolactonase 1 is more readily induced by cello-oligosaccharides, such as cellulose, than is *S. thermophile* extracellular aldonolactonase 2. Thus, *S. thermophile* extracellular aldonolactonase 1 is better suited for use in the process of degrading cello-oligosaccharide-containing biomass.

REFERENCES

1. Perlack, R. D. W., Lynn L.; Turhollow, Anthony F.; Graham, Robin L.; Stokes, Bryce J.; Erbach, Donald C. (2005) Biomass as Feedstock for A Bioenergy and Bioproducts Industry: The Technical Feasibility of a Billion-Ton Annual Supply, (Laboratory, O. R. N., Ed.), DOE, Oak Ridge, Tenn.
2. Aden, A., and Foust, T. (2009) Technoeconomic analysis of the dilute sulfuric acid and enzymatic hydrolysis process for the conversion of corn stover to ethanol, *Cellulose* 16, 535-545.
3. Bhat, K. M., and Maheshwari, R. (1987) Sporotrichum-thermophile growth, cellulose degradation, and cellulase activity, *Appl. Environ. Microbiol.* 53, 2175-2182.
4. Katapodis, P., Vrsanska, M., Kekos, D., Nerinckx, W., Biely, P., Claeyssens, M., Macris, B. J., and Christakopoulos, P. (2003) Biochemical and catalytic properties of an endoxylanase purified from the culture filtrate of Sporotrichum thermophile, *Carbohydr. Res.* 338, 1881-1890.
5. Canevascini, G., Borer, P., and Dreyer, J. L. (1991) Cellobiose dehydrogenases of Sporotrichum-(chrysosporium)-thermophile *Eur. J. Biochem.* 198, 43-52.
6. Zamocky, M., Ludwig, R., Peterbauer, C., Hallberg, B. M., Divne, C., Nicholls, P., and Haltrich, D. (2006) Cellobiose dehydrogenase—A flavocytochrome from wood-degrading, phytopathogenic and saprotropic fungi, *Curr. Protein Pept. Sci.* 7, 255-280.
7. Conchie, J., and Levvy, G. A. (1957) Inhibition of glycosidases by aldonolactones of corresponding configuration, *Biochem. J.* 65, 389-395.
8. Parry, N. J., Beever, D. E., Owen, E., Vandenberghe, I., Van Beeumen, J., and Bhat, M. K. (2001) Biochemical characterization and mechanism of action of a thermostable beta-glucosidase purified from Thermoascus aurantiacus, *Biochem. J.* 353, 117-127.
9. Iyayi, C. B., Bruchmann, E. E., and Kubicek, C. P. (1989) Induction of cellulase formation in *Trichoderma-reesei* by cellobiono-1,5-lactone, *Arch. Microbiol.* 151, 326-330.
10. Sawyer, D. T., and Bagger, J. B. (1959) The lactone acid salt equilibria for D-glucono-delta-lactone and the hydrolysis kinetics for this lactone, *J. Am. Chem. Soc.* 81, 5302-5306.
11. Collard, F., Collet, J. F., Gerin, I., Veiga-da-Cunha, M., and Van Schaftingen, E. (1999) Identification of the cDNA en coding human 6-phosphogluconolactonase, the enzyme catalyzing the second step of the pentose phosphate pathway, *FEBS Lett.* 459, 223-226.
12. Hager, P. W., Calfee, M. W., and Phibbs, P. V. (2000) The *Pseudomonas aeruginosa* devB/SOL homolog, pgl, is a member of the hex regulon and encodes 6-phosphogluconolactonase, *Journal of Bacteriology* 182, 3934-3941.
13. Zimenkov, D., Gulevich, A., Skorokhodova, A., Biriukova, I., Kozlov, Y., and Mashko, S. (2005) *Escherichia coli* ORF ybhE is pgl gene encoding 6-phosphogluconolactonase (EC 3.1.1.31) that has no homology with known 6PGLs from other organisms, *Fems Microbiology Letters* 244, 275-280.
14. Thomason, L. C., Court, D. L., Datta, A. R., Khanna, R., and Rosner, J. L. (2004) Identification of the *Escherichia coli* K-12 ybhE gene as pgl, encoding 6-phosphogluconolactonase, *Journal of Bacteriology* 186, 8248-8253.
15. Kupor, S. R., and Fraenkel, D. G. (1969) 6-phosphogluconolactonase mutants of *Escherichia coli* and a maltose blue gene, *Journal of Bacteriology* 100, 1296-1301.
16. Bruchmann, E. E., Schach, H., and Graf, H. (1987) Role and properties of lactonase in a cellulase system, *Biotechnology and Applied Biochemistry* 9, 146-159.
17. Westermark, U., and Eriksson, K. E. (1974) Cellobiose-quinone oxidoreductase, a new wood-degrading enzyme from white-rot fungi, *Acta Chemica Scandinavica Series B-Organic Chemistry and Biochemistry B* 28, 209-214.
18. Isbell, H. S. and Frush, H. L. (1963) Lactonization of aldonic acids, *Methods in Carbohydrate Chemistry* 2, 16-18.
19. Margolin, B. S., Freitag, M., and Selker, E. U. (1997) Improved plasmids for gene targeting at the his-3 locus of *Neurospora crassa* by electroporation, *Fungal Genetics Newsletter* 44, 34-36.
20. Vogel, H. (1956) A convenient growth medium for *Neurospora*, *Microbiology Genetics Bulletin* 13, 42-43.
21. Hestrin, S. (1949) The reaction of acetylcholine and other carboxylic acid derivatives with hydroxylamine, and its analytical application, *Journal of Biological Chemistry* 180, 249-261.
22. Tian, C. G., Beeson, W. T., Iavarone, A. T., Sun, J. P., Marletta, M. A., Cate, J. H. D., and Glass, N. L. (2009) Systems analysis of plant cell wall degradation by the model filamentous fungus *Neurospora crassa*, *Proceedings of the National Academy of Sciences of the United States of America* 106, 22157-22162.
23. Altschul, S. F., Madden, T. L., Schaffer, A. A., Zhang, J. H., Zhang, Z., Miller, W., and Lipman, D. J. (1997) Gapped BLAST and PSI-BLAST: a new generation of protein database search programs, *Nucleic Acids Research* 25, 3389-3402.
24. Notredame, C., Higgins, D. G., and Hering a, J. (2000) T-Coffee: A novel method for fast and accurate multiple sequence alignment, *Journal of Molecular Biology* 302, 205-217.
25. Dereeper, A., Guignon, V., Blanc, G., Audic, S., Buffet, S., Chevenet, F., Dufayard, J. F., Guindon, S., Lefort, V., Lescot, M., Clayerie, J. M., and Gascuel, O. (2008) Phylogeny.fr: robust phylogenetic analysis for the non-specialist, *Nucleic Acids Research* 36, W465-W469.
26. Tian, C. G., Kasuga, T., Sachs, M. S., and Glass, N. L. (2007) Transcriptional profiling of cross pathway control in *Neurospora crassa* and comparative analysis of the Gcn4 and CPC1 regulons, *Eukaryotic Cell* 6, 1018-1029.
27. Li, H., Ruan, J., and Durbin, R. (2008) Mapping short DNA sequencing reads and calling variants using mapping quality scores, *Genome Research* 18, 1851-1858.
28. Mortazavi, A., Williams, B. A., McCue, K., Schaeffer, L., and Wold, B. (2008) Mapping and quantifying mammalian transcriptomes by RNA-Seq, *Nature Methods* 5, 621-628.

29. Bendtsen, J. D., Nielsen, H., von Heijne, G., and Brunak, S. (2004) Improved prediction of signal peptides: SignalP 3.0, *Journal of Molecular Biology* 340, 783-795.
30. Prediction of N-glycosylation sites in human proteins., http://www.cbs.dtu.dk/services/NetNGlyc/
31. Finn, R. D., Mistry, J., Tate, J., Coggill, P., Heger, A., Pollington, J. E., Gavin, O. L., Gunasekaran, P., Ceric, G., Forslund, K., Holm, L., Sonnhammer, E. L. L., Eddy, S. R., and Bateman, A. (2010) The Pfam protein families database, *Nucleic Acids Research* 38, D211-D222.
32. Kajander, T., Merckel, M. C., Thompson, A., Deacon, A. M., Mazur, P., Kozarich, J. W., and Goldman, A. (2002) The structure of *Neurospora crassa* 3-carboxy-cis,cis-muconate lactonizing enzyme, a beta propeller cycloisomerase, *Structure* 10, 483-492.
33. Mazur, P., Henzel, W. J., Mattoo, S., and Kozarich, J. W. (1994) 3-carboxy-cis,cis-muconate lactonizing enzyme from *Neurospora-crassa*—An alternate cycloisomerase motif, *Journal of Bacteriology* 176, 1718-1728.
34. Tarighi, S., Wei, Q., Camara, M., Williams, P., Fletcher, M. P., Kajander, T., and Cornelis, P. (2008) The PA4204 gene encodes a periplasmic gluconolactonase (PpgL) which is important for fitness of *Pseudomonas aeruginosa*, *Microbiology-Sgm* 154, 2979-2990.
35. Claeyssens, M., Vantilbeurgh, H., Tomme, P., Wood, T. M., and McRae, S. I. (1989) Fungal cellulase systems—Comparison of the specificities of the cellobiohydrolases isolated from *Penicillium-pinophilum* and *Trichoderma-reesei*, *Biochem. J.* 261, 819-825.

What is claimed is:

1. A method of producing aldonic acid comprising contacting a hexose-δ-lactone substrate with a recombinant polypeptide comprising a polypeptide having at least 90% sequence identity to SEQ ID NO: 2 wherein said polypeptide has lactonase activity.

2. The method of claim 1, wherein the recombinant polypeptide comprises a polypeptide having at least 95% sequence identity to SEQ ID NO: 2.

3. The method of claim 1, wherein the recombinant polypeptide comprises a polypeptide having at least 99% sequence identity to SEQ ID NO: 2.

4. The method of claim 1, wherein the recombinant polypeptide comprises SEQ ID NO: 2.

5. The method of claim 1, wherein the hexose-δ-lactone substrate is cellobiono-δ-lactone.

6. The method of claim 1, wherein the hexose-δ-lactone substrate is glucono-δ-lactone.

7. The method of claim 1, wherein the hexose-δ-lactone substrate is lactono-δ-lactone.

8. The method of claim 2, wherein the hexose-δ-lactone substrate is cellobiono-δ-lactone.

9. The method of claim 2, wherein the hexose-δ-lactone substrate is glucono-δ-lactone.

10. The method of claim 2, wherein the hexose-δ-lactone substrate is lactono-δ-lactone.

11. The method of claim 3, wherein the hexose-δ-lactone substrate is cellobiono-δ-lactone.

12. The method of claim 3, wherein the hexose-δ-lactone substrate is glucono-δ-lactone.

13. The method of claim 3, wherein the hexose-δ-lactone substrate is lactono-δ-lactone.

14. The method of claim 4, wherein the hexose-δ-lactone substrate is cellobiono-δ-lactone.

15. The method of claim 4, wherein the hexose-δ-lactone substrate is glucono-δ-lactone.

16. The method of claim 4, wherein the hexose-δ-lactone substrate is lactono-δ-lactone.

* * * * *

SEQUENCE LISTING

```
<160> NUMBER OF SEQ ID NOS: 16

<210> SEQ ID NO 1
<211> LENGTH: 400
<212> TYPE: PRT
<213> ORGANISM: Sporotrichum thermophile
<220> FEATURE:
<223> OTHER INFORMATION: extracellular aldonolactonase 1

<400> SEQUENCE: 1

Met Arg Thr Ser Tyr Gly Val Ala Phe Ala Leu Ser Ala Gly Phe Arg
 1               5                  10                  15

Leu Ala Thr Ala Ala Pro Val Cys Gly Gly Ser Ala Ser Asp Leu
                20                  25                  30

Leu Trp Val Thr Thr Tyr Pro Ala Gly Glu Gly Ala Gln Gly Lys Leu
                35                  40                  45

Leu Thr Leu Lys Leu Asp Gly Ser Lys Leu Val Val Ala Glu Ser Asp
        50                  55                  60

Thr Cys Gly Pro Tyr Pro Ser Trp Leu Thr Gln Ala Gly Asp Val Leu
65                  70                  75                  80

Tyr Cys Val Asp Glu Ala Trp Gly Gly Asp His Gly Thr Leu His Ser
                85                  90                  95

Leu Lys Ile Asn Asp Asp His Ser Phe Thr Asn Leu Ser Gln His Glu
                100                 105                 110

Thr Val Gly Gly Pro Val Ser Thr Val Ile Tyr Gly Lys Asp Gly Leu
            115                 120                 125

Gly Leu Ala Val Ala Asp Tyr Ala Gly Gly Ile Asp Thr Phe Asn
        130                 135                 140

Ile Ala Asp Pro Ala Ala Ile Lys Leu Ile Lys Ser Leu Val Tyr Pro
145                 150                 155                 160

Ala Pro Thr Asp Gly Leu Pro Asp Pro Gln Asn Ser Ala Arg Pro His
                165                 170                 175

Glu Ala Ile Leu Asp Pro Thr Gly Glu Phe Leu Val Phe Pro Asp Leu
                180                 185                 190

Gly Ala Asp Gln Ile Arg Val Leu Lys Val Asp Lys Glu Thr Leu Glu
            195                 200                 205

Tyr Val Glu Lys Pro Ser Tyr Thr Asp Phe Asp Arg Gly Thr Gly Pro
        210                 215                 220

Arg His Gly Ala Phe Phe Lys Ser Gly Asp Lys Thr Phe Phe Tyr Leu
225                 230                 235                 240

Val Gly Glu Leu Ser Asn Leu Leu Gln Gly Phe Ser Val Ala Tyr Asn
                245                 250                 255
```

```
Asp Asp Asp Ser Leu Thr Phe Thr Arg Ile His Asn Ser Thr Thr His
            260                 265                 270

Gly Asp Asp Lys Pro Leu Pro Glu Asp Thr Ala Ala Ala Glu Leu Trp
            275                 280             285

Ile Ala Pro Gly Ser Asn Phe Leu Thr Leu Ser Ser Arg Phe Glu Ser
290                 295                 300

Ser Leu Glu Tyr Thr Val Ala Asn Gly Thr Lys Val Pro Ser Asp Pro
305                 310                 315                 320

Leu Ile Thr Phe Ser Ile Asp Lys Glu Thr Gly Ala Leu Thr His Val
                325                 330                 335

Gln Ser Ala Pro Ala Gly Gly Ile Asn Pro Arg His Phe Ser Phe Asn
            340                 345                 350

Ser Asp Gly Thr Arg Val Ala Ser Ala Leu Gln Ser Asp Gly Arg Val
            355                 360                 365

Val Val Phe Glu Arg Asp Pro Ser Thr Gly Lys Ile Gly Lys Ala Thr
370                 375                 380

Ala Glu Gly Asp Val Glu Gly Met Pro Asn Phe Ala Thr Phe Lys Gln
385                 390                 395                 400

<210> SEQ ID NO 2
<211> LENGTH: 400
<212> TYPE: PRT
<213> ORGANISM: Sporotrichum thermophile
<220> FEATURE:
<223> OTHER INFORMATION: extracellular aldonolactonase 2

<400> SEQUENCE: 2

Met Ser Pro Val Thr Gln Leu Leu Ala Ala Ala Leu Ala Leu Ala
1               5                   10                  15

Pro Gly Ala Leu Gly Ala His Leu Ile Ala Ser His Phe Ser Gly Thr
                20                  25                  30

Val Tyr Ser Leu Ser Phe Thr Ser Ser Asn Ser Thr Gly Thr Leu
                35                  40                  45

Ser Val Thr Ser Glu Thr Asp Gly Cys Gly Ala Thr Pro Ala Trp Leu
        50                  55                  60

Gln Leu Tyr Ser Asp Thr Gly Lys Val Tyr Cys Phe Asp Glu Ser Trp
65                  70                  75                  80

Leu Gly Ser Gly Ser Ser Ala Glu Tyr Glu Ile Ala Asp Asp Gly Ser
                85                  90                  95

Leu Thr Leu Thr Gly Thr Leu Gln Thr Thr Gly Asn Ser Val His Gly
                100                 105                 110

Ala Leu Tyr Gly Gly Ala Asp Gly Lys Gly Phe Val Ala Thr Val Glu
            115                 120                 125

Tyr Thr Pro Ser Thr Leu Thr Thr Tyr Lys Met Pro Phe Gly Gly Gly
            130                 135                 140

Gln Arg Leu Ala Leu Glu Lys Phe Thr Met Glu Gly Gln Gly Pro Asn
145                 150                 155                 160

Pro Arg Gln Asp Val Pro His Pro His Glu Ala Gln Val Asp Pro Thr
                165                 170                 175

Gly Asn Tyr Met Val Val Pro Asp Leu Gly Ala Asp Leu Leu Arg Val
                180                 185                 190

Phe Arg Ile Asn Ala Glu Thr Gly Glu Leu Thr Ala Cys Ser Glu Gly
            195                 200                 205

Gln Ala Gly Pro Gly Asp Gly Pro Arg His Ile Val Phe Trp Lys Asn
210                 215                 220
```

Ala Glu Gly Leu Gln Lys Ala Tyr Val Val Asn Glu Leu Gly Asn Ser
225                 230                 235                 240

Val Ser Ala Trp Asp Val Glu Tyr Pro Glu Asp Asp Asp Asp Asp Glu
                245                 250                 255

Ala Ala Ala Gly Gly Cys Leu Ala Leu Asn Lys Thr Gln Thr Leu Ser
            260                 265                 270

Thr Tyr Glu Pro Gly Thr Ser Gly Pro Thr Thr Lys Ala Ala Glu
        275                 280                 285

Ile Arg Val Val Gly Asn Phe Leu Tyr Ala Ser Asn Arg Ala Asp Glu
    290                 295                 300

Thr Phe Gly Pro Gly Gln Asp Ser Ile Ala Thr Tyr Thr Ile Asp Glu
305                 310                 315                 320

Gln Thr Gly Glu Leu Ala Trp Leu Gly Ala Ala Asn Ser Tyr Ser Tyr
                325                 330                 335

Tyr Pro Arg Thr Phe Glu Phe Asn Arg Asp Gly Thr Leu Val Ala Val
                340                 345                 350

Gly Gly Gln Thr Ser Ser Asn Val Ala Ile Ile Ala Arg Asp Pro Asp
            355                 360                 365

Thr Gly Lys Leu Gly Asn Leu Val Ala Asn Leu Glu Val Gly Arg Lys
370                 375                 380

Gly Arg Ala Gly Gln Glu Asp Gly Leu Ser Ala Val Val Trp Val Gln
385                 390                 395                 400

<210> SEQ ID NO 3
<211> LENGTH: 390
<212> TYPE: PRT
<213> ORGANISM: N. crassa
<220> FEATURE:
<223> OTHER INFORMATION: lactonase 2

<400> SEQUENCE: 3

Met Val His Leu Leu Ser Asn Leu Leu Val Gly Leu Ala Leu Ala Pro
 1               5                  10                  15

Ser Ala Leu Gly Ala Thr Leu Leu Val Ser His Phe Ser Gly Pro Val
                20                  25                  30

Tyr Thr Leu Ser Leu Thr Thr Ser Gly Thr Thr Gly Lys Leu Ser Ile
            35                  40                  45

Thr Ser Gln Ala Gly Gly Cys Gly Thr Thr Pro Ala Trp Leu Glu Tyr
 50                  55                  60

Tyr Asn Asp Thr Lys Thr Ala Tyr Cys Phe Asp Glu Ser Trp Thr Gly
 65                  70                  75                  80

Ser Gly Val Ile Thr Gln Tyr Asn Val Gly Ser Asp Gly Arg Leu Thr
                 85                  90                  95

Gln Ser Gly Gln Thr Arg Thr Ser Gly Asn Thr Val His Gly Lys Val
            100                 105                 110

Tyr Gly Gly Ser Asp Gly Lys Gly Phe Ile Ala Thr Ala Gln Tyr Ser
        115                 120                 125

Pro Ser Thr Ile Thr Thr Tyr Lys Leu Pro Leu Gly Gln Gly Gln Val
    130                 135                 140

Gln Leu Glu Lys Phe Thr Met Ser Gln Arg Gly Pro Asn Ser Arg Gln
145                 150                 155                 160

Asp Val Pro His Pro His Glu Thr Gln Leu Asp Pro Thr Gly Lys Phe
                165                 170                 175

Met Leu Val Pro Asp Leu Gly Ala Asp Leu Ile Arg Ile Phe Lys Ile
            180                 185                 190

```
Asp Ala Ser Thr Gly Arg Leu Thr Ala Cys Pro Ala Gly Gln Ala Ser
            195                 200                 205

Pro Gly Asp Gly Pro Arg His Ala Gln Trp Trp Lys Ser Ala Asp Gly
        210                 215                 220

Val Leu Arg Leu Tyr Thr Leu Asn Glu Leu Gly Asn Ser Val Ser Ser
225                 230                 235                 240

Trp Asn Val Val Tyr Pro Thr Asp Ser Asn Gly Cys Leu Ala Leu Ser
                245                 250                 255

Arg Ala Gln Thr Leu Ser Thr Tyr Ala Pro Gly Lys Lys Gly Gly Pro
            260                 265                 270

Thr Thr Lys Ala Ala Glu Ile Arg Val Ala Gly Asn Phe Leu Tyr Ala
        275                 280                 285

Ser Asn Arg Ala Asp Gln Thr Phe Gly Ser Asn Gln Asp Ser Val Ala
290                 295                 300

Ile Tyr Thr Ile Asp His Gln Thr Gly Gly Ile Ala Trp Lys Glu Ala
305                 310                 315                 320

Ala Asn Ser Tyr Ser Tyr Pro Arg Thr Phe Asp Ile Asn Lys Asp
                325                 330                 335

Gly Thr Leu Val Ala Phe Gly Gly Gln Thr Ser Ser Asn Val Ala Ile
            340                 345                 350

Val Ser Arg Asp Pro Ala Thr Gly Lys Leu Gly Asn Leu Val Ala Asn
        355                 360                 365

Leu Gln Val Gly Asn Lys Gly Arg Ala Gly Glu Glu Asp Gly Leu Ser
370                 375                 380

Ala Val Val Trp Val Glu
385                 390

<210> SEQ ID NO 4
<211> LENGTH: 379
<212> TYPE: PRT
<213> ORGANISM: Podospora anserina
<220> FEATURE:
<223> OTHER INFORMATION: aldonolactonase 1

<400> SEQUENCE: 4

Met Arg Ala Thr His Gly Ile Phe Ala Ala Leu Ser Ala Gly Leu Ser
 1               5                  10                  15

Leu Ser Ser Ala Ala Ala Cys Ser Lys Gln Gly Leu Leu Leu Val Ser
            20                  25                  30

Ser Tyr Pro Phe Glu Ser Ser Pro Gly Glu Ile Val Lys Gly Gly Val
        35                  40                  45

Thr Thr Leu Lys Leu Gly Asn Lys Gly Leu Glu Gln Val Gly Glu Ile
50                  55                  60

Ser Ser Ile Cys Gly Thr Asn Pro Ser Trp Gln Thr Leu Val Gly Gly
65                  70                  75                  80

Asp Gln Tyr Tyr Cys Ile Asn Glu Asn Phe Asp Asp Gly Pro Gly Ala
                85                  90                  95

Phe Thr Ser Ala Lys Val Asn Thr Asp Gly Thr Leu Ala Phe Val Gly
            100                 105                 110

Asn Ser Ser Thr Pro Gly Gly Pro Val His Ile Ala Leu Phe Gly Glu
        115                 120                 125

Asn Gly Glu Arg Ala Ile Thr Ser Asn Phe Ala Ser Ser Ser Leu Asp
130                 135                 140

Val Phe Asn Ile Glu Asp Pro Ala Lys Leu Gln Ser Leu Asp Asn Lys
145                 150                 155                 160
```

-continued

```
Pro Phe Pro Pro Arg Ala Asp Asn Glu Thr Ile Thr Ser Arg Pro His
                165                 170                 175
Gln Ala Val Val Asp Pro Thr Gly Gly Phe Val Val Ile Pro Asp Leu
            180                 185                 190
Ser Val Asp Val Leu His Ile Phe Ser Ile Asp Gln Thr Ala Leu Thr
        195                 200                 205
Leu Thr Glu Leu Pro Ala His Pro Phe Gly Asn Gly Thr Gly Pro Arg
    210                 215                 220
His Ala Ala Phe Leu Lys Ser Gly Asp Lys Thr Phe Leu Tyr Val Ile
225                 230                 235                 240
Ala Glu Lys Lys Val Ser Ile Leu Gly Phe Glu Val Ser Tyr Gly Thr
                245                 250                 255
Asn Ser Leu Thr Leu Ser Glu Pro Arg His Thr Gln Pro Asn Asn Lys
            260                 265                 270
Phe Leu Thr Val Ser Thr Arg Asn Glu Thr Thr Leu Glu Tyr Thr Ser
        275                 280                 285
Val Ala Asp Gly Thr Lys Ile Pro Ser Asp Ala Leu Asn Thr Phe Ser
    290                 295                 300
Ile Asp Pro Ala Thr Gly Glu Leu Thr His Val Gln Ser Ala Pro Ala
305                 310                 315                 320
Gly Gly Ser Phe Pro Arg His Phe Ser Phe Asn Lys Asp Gly Ser Leu
                325                 330                 335
Val Ala Val Ala Cys Gly Gly Glu Asn Arg Val Asn Val Phe Glu Arg
            340                 345                 350
Asp Val Gly Thr Gly Met Ile Gly Lys Ala Val Gly Glu Arg Val Leu
        355                 360                 365
Thr Thr Gln Val Asn His Val Ile Phe Lys Glu
    370                 375

<210> SEQ ID NO 5
<211> LENGTH: 399
<212> TYPE: PRT
<213> ORGANISM: Trichoderma reesei

<400> SEQUENCE: 5

Met Pro Ser Arg Arg Asn Leu Gln Lys Ser Leu Val Ser Thr Leu Leu
1               5                   10                  15
Cys Ala Gly Asn Leu Ala Ser Ala Ser Leu Val Tyr Val Ser Ser Tyr
            20                  25                  30
Ser Gln Thr Val Thr Thr Leu Asn Tyr Thr His Gly Gln Asn Thr Gly
        35                  40                  45
Ile Gln Lys Leu Asn Pro Val Ala Val Ser Gln Gly Cys Ser Asp Asn
    50                  55                  60
Pro Ser Trp Leu Thr Leu Asp Ala Pro Asp Ser Ile Leu Tyr Cys Ile
65                  70                  75                  80
Asn Glu Gly Leu Asn Thr Pro Asn Gly Ser Leu Thr Ala Phe Lys Thr
                85                  90                  95
Ser Ala Ser Gly Ser Leu Gln Gln Leu Gly Gln Ser Ser Thr Pro Asn
            100                 105                 110
Gly Pro Val Ser Gly Val Phe Gly Asn Asn Arg His Gly Leu Ala
        115                 120                 125
Val Ala His Tyr Gly Gly Ser Ala Phe Thr Thr Trp Asp Val Ser Asn
    130                 135                 140
Pro Asn Ser Leu Lys Leu Leu Gln Thr Lys Thr Phe Lys Leu Thr Gly
145                 150                 155                 160
```

```
Pro Pro Ser Arg Pro Asp Arg Gln Asp Ala Pro His Pro His Glu Ala
            165                 170                 175

Val Leu Asp Pro Thr Gly Lys Phe Leu Leu Val Pro Asp Leu Gly Met
            180                 185                 190

Asp Leu Ile His Leu Tyr Ser Phe Asp Pro Asn Thr Leu Ala Leu Lys
            195                 200                 205

Asp Ile Thr Pro Leu Ser Val Lys Pro Gly Ser Gly Pro Arg His Ile
            210                 215                 220

Thr Phe Val Val Lys Gly Ser Lys Thr Phe Ala Tyr Leu Val Thr Glu
225                 230                 235                 240

Leu Gly Asn Thr Ile Ile Gly Tyr Asp Val Thr Tyr Pro Asn Gly Gln
                245                 250                 255

Ile Lys Leu Thr Glu Ile Phe Asn Ile Pro Ser His Gly Ala Gly Pro
                260                 265                 270

Ala Glu Pro Ser Ser Tyr Ala Ala Ser Glu Val Val Ser Pro Asp
            275                 280                 285

Thr Asn Tyr Leu Ile Val Ser Ser Arg Ala Glu Asn Ser Thr Ser Ile
            290                 295                 300

Pro Asp Phe Asp Asp Pro Ser Arg Ile Ile Pro Ser Asp Pro Leu Ile
305                 310                 315                 320

Asn Phe Lys Ile Asn Pro Thr Thr Gly Gln Leu Gln Leu Leu Gln Val
                325                 330                 335

Val Pro Ala Gly Gly Gln Phe Pro Arg Gln Phe Ser Ile Asn Lys Glu
                340                 345                 350

Gly Asn Leu Leu Ala Val Gly Leu Gln Asn Asp Gly Arg Val Val Phe
            355                 360                 365

Val Asp Arg Cys Pro Glu Thr Gly Leu Leu Gly Phe Val Ala Tyr
370                 375                 380

Ala Asp Ile Glu Gly Gln Ile Thr Ala Ala Ile Phe Asp Gln Lys
385                 390                 395

<210> SEQ ID NO 6
<211> LENGTH: 417
<212> TYPE: PRT
<213> ORGANISM: Aspergillus niger

<400> SEQUENCE: 6

Met Ile Ser Phe Leu Arg Thr Leu Thr Phe Gly Leu Thr Leu Ser Ser
 1               5                  10                  15

Ala Leu Ala Lys Ser Thr Ser Ser Thr Leu Tyr Ala Thr His Tyr Ser
            20                  25                  30

Thr Ser Ser Ile Tyr Thr Leu Thr Leu Lys Gln Ser Asn Asn Thr Tyr
        35                  40                  45

Ser Leu Ala Glu Ala Ser Ser Leu Lys Thr Cys Gly Arg Tyr Pro Ser
    50                  55                  60

Trp Ile Thr Leu Asp Ala Ser Thr Lys Thr Leu Tyr Cys Ser Asp Glu
65                  70                  75                  80

Tyr Gly Trp Arg Asn Ala Gly Gly Thr Val Asn Gly Ser Leu Thr Thr
                85                  90                  95

Val Asn Val Gly Glu Asp Gly Ser Leu Ser Glu Ala Val Thr Gly
            100                 105                 110

Thr Ala Pro Gly Ser Gly Val His Asn Ile Val Tyr Glu Gly Asp Gly
            115                 120                 125

Gly Glu Lys Tyr Leu Ala Ile Ala His Tyr Ser Gly Ala Ala Val Ser
            130                 135                 140
```

```
Thr Tyr Ala Leu Pro Leu Glu Asn Asp Ala Asp Pro Leu Gln Val Phe
145                 150                 155                 160

Glu Phe Glu Leu Asp Thr Pro Gly Glu Val Pro Asp Arg Gln Glu Ala
            165                 170                 175

Pro His Pro His Gln Thr Phe Leu Asp Pro Thr Gly Ser Phe Val Leu
        180                 185                 190

Val Pro Asp Leu Gly Ala Asp Leu Ile Arg Val Phe Ala Ile Asp Lys
    195                 200                 205

Ser Asn Gly Glu Leu Asn Ala Cys Pro Ser Leu Asn Tyr Thr Leu Gly
210                 215                 220

Gly Gly Pro Arg His Gly Val Phe Arg Thr Ala Ser Asp Ser Glu Leu
225                 230                 235                 240

Arg Ile Arg Gly Arg Ala Pro Gly Pro Glu Thr Val Leu Tyr Val Thr
                245                 250                 255

Gly Glu Leu Asn Gly Glu Val Glu Ala Phe Ala Val Ser Tyr Pro Lys
            260                 265                 270

Ser Gly Cys Leu Ser Phe Glu Gln Ile Asp Thr Glu Ile Pro Tyr Pro
        275                 280                 285

Ser Asp Leu Pro Asp Gly Ala Ser Leu Ser Glu Ile Arg Leu Val Glu
290                 295                 300

Asp Asp Leu Tyr Val Ser Val Arg Leu Asp Ser Ala Phe Gly Gly Asp
305                 310                 315                 320

Asp Ser Leu Ala Arg Leu Ser Leu Arg Gln Asp Gly Lys Val Glu Phe
                325                 330                 335

Glu Glu Ile Ser Thr Ser Gly Gly Val Leu Pro Arg Thr Phe Ala Ile
            340                 345                 350

Asn Lys Ala Gly Asp Leu Val Ala Val Gly Asn Gln Leu Ser Ser Thr
        355                 360                 365

Val Thr Ile Val Glu Arg Asp Pro Glu Thr Gly Ala Leu Gly Glu Val
    370                 375                 380

Val Ala Glu Leu Leu Val Gly Glu Pro Gly Glu Pro Asn Asn Leu Glu
385                 390                 395                 400

Val Asn Gly Asn Val Asn Val Asn Gly Met Ser Thr Asp Met Gly Val
                405                 410                 415

Arg

<210> SEQ ID NO 7
<211> LENGTH: 331
<212> TYPE: PRT
<213> ORGANISM: Escherichia coli
<220> FEATURE:
<223> OTHER INFORMATION: 6-phosphogluconolactonase

<400> SEQUENCE: 7

Met Lys Gln Thr Val Tyr Ile Ala Ser Pro Glu Ser Gln Gln Ile His
1               5                   10                  15

Val Trp Asn Leu Asn His Glu Gly Ala Leu Thr Leu Thr Gln Val Val
            20                  25                  30

Asp Val Pro Gly Gln Val Gln Pro Met Val Val Ser Pro Asp Lys Arg
        35                  40                  45

Tyr Leu Tyr Val Gly Val Arg Pro Glu Phe Arg Val Leu Ala Tyr Arg
    50                  55                  60

Ile Ala Pro Asp Asp Gly Ala Leu Thr Phe Ala Ala Glu Ser Ala Leu
65                  70                  75                  80

Pro Gly Ser Pro Thr His Ile Ser Thr Asp His Gln Gly Gln Phe Val
                85                  90                  95
```

-continued

```
Phe Val Gly Ser Tyr Asn Ala Gly Asn Val Ser Val Thr Arg Leu Glu
            100                 105                 110

Asp Gly Leu Pro Val Gly Val Asp Val Val Glu Gly Leu Asp Gly
            115                 120                 125

Cys His Ser Ala Asn Ile Ser Pro Asp Asn Arg Thr Leu Trp Val Pro
130                 135                 140

Ala Leu Lys Gln Asp Arg Ile Cys Leu Phe Thr Val Ser Asp Asp Gly
145                 150                 155                 160

His Leu Val Ala Gln Asp Pro Ala Glu Val Thr Thr Val Glu Gly Ala
                165                 170                 175

Gly Pro Arg His Met Val Phe His Pro Asn Glu Gln Tyr Ala Tyr Cys
            180                 185                 190

Val Asn Glu Leu Asn Ser Ser Val Asp Val Trp Glu Leu Lys Asp Pro
            195                 200                 205

His Gly Asn Ile Glu Cys Val Gln Thr Leu Asp Met Met Pro Glu Asn
            210                 215                 220

Phe Ser Asp Thr Arg Trp Ala Ala Asp Ile His Ile Thr Pro Asp Gly
225                 230                 235                 240

Arg His Leu Tyr Ala Cys Asp Arg Thr Ala Ser Leu Ile Thr Val Phe
                245                 250                 255

Ser Val Ser Glu Asp Gly Ser Val Leu Ser Lys Glu Gly Phe Gln Pro
            260                 265                 270

Thr Glu Thr Gln Pro Arg Gly Phe Asn Val Asp His Ser Gly Lys Tyr
            275                 280                 285

Leu Ile Ala Ala Gly Gln Lys Ser His His Ile Ser Val Tyr Glu Ile
            290                 295                 300

Val Gly Glu Gln Gly Leu Leu His Glu Lys Gly Arg Tyr Ala Val Gly
305                 310                 315                 320

Gln Gly Pro Met Trp Val Val Asn Ala His
                325                 330

<210> SEQ ID NO 8
<211> LENGTH: 366
<212> TYPE: PRT
<213> ORGANISM: Neurospora crassa
<220> FEATURE:
<223> OTHER INFORMATION: cis-carboxy-muconate-lactonizing enzyme

<400> SEQUENCE: 8

Met Pro Leu His His Leu Met Ile Gly Thr Trp Thr Pro Pro Gly Ala
 1               5                  10                  15

Ile Phe Thr Val Gln Phe Asp Asp Glu Lys Leu Thr Cys Lys Leu Ile
            20                  25                  30

Lys Arg Thr Glu Ile Pro Gln Asp Glu Pro Ile Ser Trp Met Thr Phe
            35                  40                  45

Asp His Glu Arg Lys Asn Ile Tyr Gly Ala Ala Met Lys Lys Trp Ser
        50                  55                  60

Ser Phe Ala Val Lys Ser Pro Thr Glu Ile Val His Glu Ala Ser His
65                  70                  75                  80

Pro Ile Gly Gly His Pro Arg Ala Asn Asp Ala Asp Thr Asn Thr Arg
                85                  90                  95

Ala Ile Phe Leu Leu Ala Ala Lys Gln Pro Pro Tyr Ala Val Tyr Ala
            100                 105                 110

Asn Pro Phe Tyr Lys Phe Ala Gly Tyr Gly Asn Val Phe Ser Val Ser
            115                 120                 125
```

Glu Thr Gly Lys Leu Glu Lys Asn Val Gln Asn Tyr Glu Tyr Gln Glu
        130                 135                 140

Asn Thr Gly Ile His Gly Met Val Phe Asp Pro Thr Glu Thr Tyr Leu
145                 150                 155                 160

Tyr Ser Ala Asp Leu Thr Ala Asn Lys Leu Trp Thr His Arg Lys Leu
                165                 170                 175

Ala Ser Gly Glu Val Glu Leu Val Gly Ser Val Asp Ala Pro Asp Pro
            180                 185                 190

Gly Asp His Pro Arg Trp Val Ala Met His Pro Thr Gly Asn Tyr Leu
        195                 200                 205

Tyr Ala Leu Met Glu Ala Gly Asn Arg Ile Cys Glu Tyr Val Ile Asp
    210                 215                 220

Pro Ala Thr His Met Pro Val Tyr Thr His His Ser Phe Pro Leu Ile
225                 230                 235                 240

Pro Pro Gly Ile Pro Asp Arg Asp Pro Glu Thr Gly Lys Gly Leu Tyr
                245                 250                 255

Arg Ala Asp Val Cys Ala Leu Thr Phe Ser Gly Lys Tyr Met Phe Ala
            260                 265                 270

Ser Ser Arg Ala Asn Lys Phe Glu Leu Gln Gly Tyr Ile Ala Gly Phe
        275                 280                 285

Lys Leu Arg Asp Cys Gly Ser Ile Glu Lys Gln Leu Phe Leu Ser Pro
    290                 295                 300

Thr Pro Thr Ser Gly Gly His Ser Asn Ala Val Ser Pro Cys Pro Trp
305                 310                 315                 320

Ser Asp Glu Trp Met Ala Ile Thr Asp Asp Gln Glu Gly Trp Leu Glu
                325                 330                 335

Ile Tyr Arg Trp Lys Asp Glu Phe Leu His Arg Val Ala Arg Val Arg
            340                 345                 350

Ile Pro Glu Pro Gly Phe Gly Met Asn Ala Ile Trp Tyr Asp
        355                 360                 365

<210> SEQ ID NO 9
<211> LENGTH: 4
<212> TYPE: PRT
<213> ORGANISM: Sporotrichum thermophile
<220> FEATURE:
<223> OTHER INFORMATION: aldonolactonase 1 motif

<400> SEQUENCE: 9

Gly Pro Arg His
 1

<210> SEQ ID NO 10
<211> LENGTH: 7
<212> TYPE: PRT
<213> ORGANISM: Sporotrichum thermophile
<220> FEATURE:
<223> OTHER INFORMATION: aldonolactonase 1 motif
<220> FEATURE:
<221> NAME/KEY: Variant
<222> LOCATION: 5
<223> OTHER INFORMATION: Xaa = Any amino acid

<400> SEQUENCE: 10

Asp Pro Thr Gly Xaa Phe Tyr
 1               5

<210> SEQ ID NO 11
<211> LENGTH: 32
<212> TYPE: DNA
<213> ORGANISM: Neurospora crassa

```
<220> FEATURE:
<223> OTHER INFORMATION: NCU07143 forward primer

<400> SEQUENCE: 11
atatatatgg taccgccact ttgctggttt cc                                    32

<210> SEQ ID NO 12
<211> LENGTH: 40
<212> TYPE: DNA
<213> ORGANISM: Neurospora crassa
<220> FEATURE:
<223> OTHER INFORMATION: NCU07143 reverse primer

<400> SEQUENCE: 12
atatatattc tagattctct acccaaacga cagcactaag                            40

<210> SEQ ID NO 13
<211> LENGTH: 29
<212> TYPE: DNA
<213> ORGANISM: Sporotrichum thermophile
<220> FEATURE:
<223> OTHER INFORMATION: aldonolactonase 1 forward primer

<400> SEQUENCE: 13
atatatatgg taccgccccg gtctgtggc                                        29

<210> SEQ ID NO 14
<211> LENGTH: 38
<212> TYPE: DNA
<213> ORGANISM: Sporotrichum thermophile
<220> FEATURE:
<223> OTHER INFORMATION: aldonolactonase 1 reverse primer

<400> SEQUENCE: 14
atatatattc tagattctgc ttaaacgtgg caaagttg                              38

<210> SEQ ID NO 15
<211> LENGTH: 22
<212> TYPE: DNA
<213> ORGANISM: Sporotrichum thermophile
<220> FEATURE:
<223> OTHER INFORMATION: aldonolactonase 2 forward primer

<400> SEQUENCE: 15
tacttccaat ccaatgcaat gt                                               22

<210> SEQ ID NO 16
<211> LENGTH: 21
<212> TYPE: DNA
<213> ORGANISM: Sporotrichum thermophile
<220> FEATURE:
<223> OTHER INFORMATION: aldonolactonase 2 reverse primer

<400> SEQUENCE: 16
ctcccactac caatgccctg c                                                21
```